(12) United States Patent
Meisler et al.

(10) Patent No.: US 9,365,899 B2
(45) Date of Patent: Jun. 14, 2016

(54) FIG4 GENE MUTATIONS IN NEURODEGENERATION

(75) Inventors: Miriam Meisler, Ann Arbor, MI (US); James R. Lupski, Houston, TX (US); Clement Y. Chow, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 346 days.

(21) Appl. No.: 12/597,539

(22) PCT Filed: Apr. 25, 2008

(86) PCT No.: PCT/US2008/061616
§ 371 (c)(1),
(2), (4) Date: Feb. 1, 2010

(87) PCT Pub. No.: WO2008/134539
PCT Pub. Date: Nov. 6, 2008

(65) Prior Publication Data
US 2010/0143255 A1 Jun. 10, 2010

Related U.S. Application Data

(60) Provisional application No. 60/926,276, filed on Apr. 26, 2007.

(51) Int. Cl.
*C12Q 1/68* (2006.01)
*C12P 19/34* (2006.01)
*C07H 21/02* (2006.01)

(52) U.S. Cl.
CPC ........ *C12Q 1/6883* (2013.01); *C12Q 2600/156* (2013.01); *C12Q 2600/158* (2013.01); *C12Q 2600/172* (2013.01); *G01N 2500/10* (2013.01)

(58) Field of Classification Search
None
See application file for complete search history.

(56) References Cited

U.S. PATENT DOCUMENTS

| | | | | |
|---|---|---|---|---|
| 5,550,020 A | * | 8/1996 | Gallie et al. | 435/6.12 |
| 5,714,325 A | * | 2/1998 | Bianchi | 435/6.16 |
| 7,504,227 B2 | | 3/2009 | Muchowski | |
| 2003/0092019 A1 | * | 5/2003 | Meyer et al. | 435/6 |
| 2005/0059067 A1 | * | 3/2005 | Smith | 435/6 |
| 2006/0084071 A1 | * | 4/2006 | Muchowski | 435/6 |
| 2007/0292859 A1 | * | 12/2007 | Kozian et al. | 435/6 |

FOREIGN PATENT DOCUMENTS

| CA | 2399280 | 7/2002 |
|---|---|---|

OTHER PUBLICATIONS

Gary, Jonathan et al. Regulation of Fab1 phosphatidylinositol 3-phosphate 5 kinase pathway by Vac 7 protien and Fig4, a polyphosphoinositide phosphatase family member. Molecular Biology of the Cell Apr. 2002 vol. 13 pp. 1238-1251.*
Gene Card for FIG4 http://www.genecards.org/cgi-bin/carddisp.pl?gene=FIG4&search=fig4 accessed online Jan. 19, 2012.*
Mummidi et al Evolution of human and non human primate CC chemokine receptor 5 gene and mRNA. Journal of Biological Chemistry 2000 vol. 275, No. 25, pp. 18946-18961.*
Hegele. Arterioscler Thromb Vasc Biol. 2002; 22:1058-1061.*
Wacholder, Sholom et al. Assessing the probability that a positive report is false: an approach for molecular epidemiology studies. Journal of the National Cancer Institute. 2004. vol. 96 pp. 434-442.*
Hirschhorn et al. Genetics in Medicine. vol. 4, No. 2, pp. 45-61, Mar. 2002.*
Reilly et al Journal of the Peripheral Nervous System 2001 vol. 16 pp. 1-14.*
GenBank (Accession NM_014845 GI: 36030904 Sep. 26, 2003).*
Okazaki et al, "Prediction of the Coding Sequences of Mouse Homologues of KIAA Gene: IV. The Complete Nucleotide Sequences of 500 Mouse KIAA—Homologous CDNAs Identified by Screening of Terminal Sequences of CDNA Clones Randomly Sampled From Size-Fractionated Libraries," DNA Res, 11, 205-18 (2004).
Hughes et al, "SAC Phosphatase Domain Proteins," Biochem J 350 Pt. 2, 337-52 (2000).
Rudge et al., "Vacuole Size Control: Regulation of PTDINs(3,5) P2 Levels by the Vacuole-Associated VAC14-FIG4 Complex, A PTDINs(3,5)P2-Specific Phosphatase," Mol Biol Cell 15, 24-36.
Duex et al, "Phosphoinositide 5-Phosphatase FIG4P Is Required for Both Acute Rise and Subsequent Fall in Stress-Induced Phosphatidylinositol," Eukaryot Cell 5, 723-31 (2006).
Duex et al., "The VAC 14P-FIG4P Complex Acts Independently of VAC7P and Couples P13, 5P2 Synthesis and Turnover," J Cell Biol 172, 693-704 (2006).
Bonangelino et al., "Osmotic Stress-Induced Increase of Phosphatidylinositol 3,5-Bisphosphate Requires VAC14P, an Activator of the Lipid Kinase FAB1P," J Cell Biol 156, 1015-28 (2002).
Schroder, "Neuropathy of Charcot-Marie-Tooth and Related Disorders," Neuromolecular Med 8, 23-42 (2006).
Szigeti et al., "Charcot-Marie-Tooth Disease and Related Hereditary Polyneuropathies: Molecular Diagnostics Determine Aspects of Medical Management," Genet Med 8, 96-92 (2006).
Begley Eta al., "Molecular Basis for Substrate Recognition by MTMR2, a Myotubularin Family Phosphoinositide Phosphatase ," Proc Natl Acad Sci USA 103, 927-32 (2006).
Bolino et al., "Disruption of MTMR2 Produces CMT4B1—Like Neuropathy With Myelin Outfolding and Impaired Spermatogenesis," J Cel Biol 167, 711-21 (2004).
Bonneick et al., "An Animal Model for Charcot-Marie Tooth Disease Type 4B1," Hum Mol Genet 14, 3685-95 (2005).

(Continued)

*Primary Examiner* — Amanda Haney
(74) *Attorney, Agent, or Firm* — Casimir Jones, S.C.; Tanya Arenson; David Casimir

(57) ABSTRACT

The present invention relates to neuropathy, in particular to mutations in the FI G4 gene. The present invention also provides assays for the detection of variant FIG4 alleles, and assays for detecting FIG4 polymorphisms and mutations associated with disease states.

16 Claims, 13 Drawing Sheets

(56) References Cited

OTHER PUBLICATIONS

Verhoeven et al., "Mutations in the Small GTP-ASE Late Endosomal Protein RAB7 Cause Charcot-Marie-Tooth Type 2B Neuropathy," Am J. Hum Genet 72, 722-7 (2003).

Zuchner et al, "Mutations in the Pleckstrin Homology Domain of Dynamin 2 Cause Dominant Intermediate Charcot-Marie-Tooth Disease," Nat Genet 37, 289-94 (2005).

Lemaire and McPherson, "Binding of VAC14 to Neuronal Nitric Oxide Synthase: Characterisation of a New Internal PDZ-Recognition Motif," FEBS Lett V. 580, p. 6948-6954 (2006).

Park et al., "Plasticity-Induced Growth of Dendritic Spines by Exocytic Trafficking From Recycling Endosomes," Neuron 52, 817-30 (2006).

Clement Chow et al, "Mutation of FIG4 Causes Neurodengeneration in the Pale Tremor Mouse and Patient With CMT4J," Nature Jul. 5, 2007, vol. 448, p. 68-72.

Gary et al., "Regulation of FAB1 Phosphatidylinositol 3-Phosphate 5-Kinase Pathway by VAC7 Protein and FIG4, a Polyphosphoinositide Phosphatase Family Member," Mol Biol Cell 13, 1238-51 (2002).

* cited by examiner

Figure 13

FIG4 human cDNA

I41T mutation is c122T>C

GGAGGCGGGGCGCAGGGATCCGGAAACACCTGATCATCTATAGGTTTAGTGCCTAATGGG
TGTTGTTCCTGGCTGGACTTGATGTCCAGGGCCTGAGGGGTTTTCTCGCCGAGTCTCCTG
GGGCGGTCCGGAGGCTCGTGCCCTGTTGTGGGGCCCCCATTTGCCGCCGCCATGCCCACG
GCCGCCGCCCCCATCATCAGCTCGGTCCAGAAGCTGGTTCTGTATGAGACTAGAGCTAGA
TACTTTCTAGTTGGGAGCAATAATGCAGAAACGAAATATCGTGTCTTGAAGATTGATAGA
ACAGAACCAAAAGATTTGGTCATAATTGATGACAGGCATGTCTATACTCAACAAGAAGTA
AGGGAACTTCTTGGCCGCTTGGATCTTGGAAATAGAACAAAGATGGGACAGAAAGGATCC
TCGGGCTTATTTCGAGCGGTTTCAGCTTTTGGTGTTGTGGGTTTTGTCAGGTTCTTAGAA
GGCTATTATATTGTGTTAATAACTAAAAGGAGGAAGATGGCGGATATTGGAGGTCATGCA
ATCTATAAGGTCGAAGATACAAATATGATCTATATACCCAATGATTCTGTACGGGTTACT
CATCCTGATGAAGCTAGGTATCTACGAATATTTCAAAATGTGGACCTATCTAGCAATTTT
TACTTTAGTTACAGCTATGATTTGTCCCACTCACTTCAATATAATCTCACTGTCTTGCGA
ATGCCCCTGGAGATGTTAAAGTCAGAAATGACCCAGAATCGCCAAGAGAGCTTTGACATC
TTTGAAGATGAAGGATTAATTACACAAGGTGGAAGCGGGGTATTTGGGATCTGTAGTGAG
CCTTATATGAAATATGTATGGAATGGTGAACTTCTGGATATAATTAAAAGTACTGTGCAT
CGTGACTGGCTTTTGTATATTATTCATGGGTTCTGTGGGCAGTCAAAGCTGTTGATCTAT
GGACGACCAGTGTATGTCACTCTAATAGCTAGAAGATCCAGTAAATTTGCTGGCACCCGT
TTTCTTAAAAGAGGTGCAAACTGTGAGGGTGATGTTGCAAATGAAGTGGAGACTGAACAA
ATACTCTGCGATGCTTCTGTGATGTCTTTCACTGCAGGAAGTTATTCTTCATATGTACAA
GTTAGAGGATCTGTGCCCTTATACTGGTCTCAGGACATTTCAACTATGATGCCTAAACCA
CCTATTACATTGGATCAGGCAGATCCATTTGCACATGTGGCTGCCCTTCACTTTGACCAG
ATGTTCCAGAGGTTTGGCTCTCCCATCATCATCTTGAATTTAGTGAAGGAACGAGAGAAA
AGAAAGCATGAAAGAATTCTGAGTGAAGAACTTGTTGCTGCTGTGACCTATCTCAACCAA
TTTTTGCCTCCTGAGCACACTATTGTTTATATTCCCTGGGACATGGCCAAGTATACCAAA
AGCAAGCTGTGTAATGTTCTTGATCGACTAAATGTGATTGCAGAAAGTGTGGTGAAGAAA
ACAGGTTTCTTTGTAAACCGCCCTGATTCTTACTGTAGCATTTTGCGGCCAGATGAAAAG
TGGAATGAACTAGGAGGATGTGTGATTCCCACTGGTCGCCTGCAGACTGGCATCCTTCGA
ACCAACTGTGTGGACTGTTTAGATCGCACCAACACAGCACAGTTTATGGTGGGAAAATGT
GCTCTGGCCTATCAGCTGTATTCACTGGGACTGATTGACAAACCTAATCTACAGTTTGAT
ACAGATGCAGTTAGGTTATTTGAGGAACTCTATGAAGATCATGGTGATACCCTATCCCTT
CAGTATGGTGGTTCTCAACTTGTTCATCGTGTGAAAACCTACAGAAAGATAGCACCATGG
ACCCAGCACTCCAAAGACATCATGCAAACCCTGTCTAGATATTACAGCAATGCTTTTTCA
GATGCCGATAGACAAGATTCCATTAATCTCTTCCTGGGAGTTTTCCATCCCACTGAAGGG
AAACCTCATCTCTGGGAGCTCCCAACAGATTTTTATTTGCATCACAAAAATACCATGAGA
CTTTTGCCAACAAGAAGAAGTTATACTTACTGGTGGACACCAGAGGTGATAAAGCATTTA
CCATTGCCCTATGATGAAGTTATCTGTGCTGTGAACTTAAAGAAGTTGATAGTGAAGAAA
TTCCACAAATATGAAGAAGAGATTGATATCCACAATGAGTTCTTTCGGCCATATGAGTTG
AGCAGCTTTGATGATACCTTTTGCTTGGCTATGACAAGCTCAGCACGTGACTTTATGCCT
AAGACCGTTGGAATTGATCCAAGTCCATTTACTGTGCGTAAACCAGATGAAACTGGAAAA
TCAGTATTGGGAAACAAAAGCAATAGAGAAGAAGCTGTATTACAGCGGAAAACGGCAGCC
AGCGCCCCGCCGCCCCCCAGCGAGGAGGCTGTGTCCAGCAGCTCTGAGGATGACTCTGGG
ACTGATCGGGAAGAAGAGGGCTCTGTGTCTCAGCGCTCCACTCCCGTGAAGATGACTGAT
GCAGGAGACAGTGCCAAAGTGACCGAGAATGTGGTCCAACCCATGAAGGAGCTATATGGA
ATTAACCTCTCAGATGGCCTCTCAGAAGAAGATTTCTCCATTTATTCAAGATTTGTTCAG
CTGGGGCAGAGTCAACATAAACAAGACAAGAATAGCCAGCAGCCCTGTTCTAGGTGCTCA
GATGGAGTTATAAAACTAACACCCATCTCGGCTTTCTCGCAAGATAACATCTATGAAGTT
CAGCCCCCAAGAGTAGACAGAAAATCTACAGAGATCTTCCAAGCCCACATCCAGGCCAGC
CAAGGTATCATGCAGCCCCTAGGAAAAGAGGACTCCTCCATGTACCGAGAGTACATCAGG
AACCGCTACCTGTGAAAAGAGCGCAGGTCCACCTGGTGGACACGTCTGATTAGCTTAGAA
CCTGTCTTGTCTCATCTTCAAAAGGTAACTTATTAAAAGTCCTTTGCGTCTGAAGCCTTT
CTCCTTTTCTGTCACTTGCAAATTCCAAATTATAGCTAATAAAGATGACTAGATAATTTG
C

SEQUENCE LISTING

```
<160> NUMBER OF SEQ ID NOS: 12

<210> SEQ ID NO 1
<211> LENGTH: 3061
<212> TYPE: DNA
<213> ORGANISM: Homo sapiens
```

<400> SEQUENCE: 1

```
ggaggcgggg cgcagggatc cggaaacacc tgatcatcta taggtttagt gcctaatggg      60
tgttgttcct ggctggactt gatgtccagg gcctgagggg ttttctcgcc gagtctcctg     120
gggcggtccg gaggctcgtg ccctgttgtg gggcccccat tgccgccgc catgcccacg      180
gccgccgccc ccatcatcag ctcggtccag aagctggttc tgtatgagac tagagctaga    240
tactttctag ttgggagcaa taatgcagaa acgaaatatc gtgtcttgaa gattgataga    300
acagaaccaa aagatttggt cataattgat gacaggcatg tctatactca acaagaagta    360
agggaacttc ttggccgctt ggatcttgga aatagaacaa agatgggaca gaaaggatcc    420
tcgggcttat ttcgagcggt ttcagctttt ggtgttgtgg gttttgtcag gttcttagaa    480
ggctattata ttgtgttaat aactaaaagg aggaagatgg cggatattgg aggtcatgca    540
atctataagg tcgaagatac aaatatgatc tatataccca atgattctgt acgggttact    600
catcctgatg aagctaggta tctacgaata tttcaaaatg tggacctatc tagcaatttt    660
tactttagtt acagctatga tttgtcccac tcacttcaat ataatctcac tgtcttgcga    720
atgcccctgg agatgttaaa gtcagaaatg acccagaatc gccaagagag ctttgacatc    780
tttgaagatg aaggattaat tacacaaggt ggaagcgggg tatttgggat ctgtagtgag    840
ccttatatga aatatgtatg gaatggtgaa cttctggata taattaaaag tactgtgcat    900
cgtgactggc ttttgtatat tattcatggg ttctgtgggc agtcaaagct gttgatctat    960
ggacgaccag tgtatgtcac tctaatagct agaagatcca gtaaatttgc tggcacccgt   1020
tttcttaaaa gaggtgcaaa ctgtgagggt gatgttgcaa atgaagtgga gactgaacaa   1080
atactctgcg atgcttctgt gatgtctttc actgcaggaa gttattcttc atatgtacaa   1140
gttagaggat ctgtgccctt atactggtct caggacattt caactatgat gcctaaacca   1200
cctattacat tggatcaggc agatccattt gcacatgtgg ctgcccttca cttgaccag    1260
atgttccaga ggtttggctc tcccatcatc atcttgaatt tagtgaagga acgagagaaa   1320
agaaagcatg aaagaattct gagtgaagaa cttgttgctg ctgtgaccta tctcaaccaa   1380
tttttgcctc ctgagcacac tattgtttat attccctggg acatggccaa gtataccaaa   1440
agcaagctgt gtaatgttct tgatcgacta aatgtgattg cagaaagtgt ggtgaagaaa   1500
acaggttct ttgtaaaccg ccctgattct tactgtagca ttttgcggcc agatgaaaag   1560
tggaatgaac taggaggatg tgtgattccc actggtcgcc tgcagactgg catccttcga   1620
accaactgtg tggactgttt agatcgcacc aacacagcac agtttatggt gggaaaatgt   1680
gctctggcct atcagctgta ttcactggga ctgattgaca aacctaatct acagtttgat   1740
acagatgcag ttaggttatt tgaggaactc tatgaagatc atggtgatac cctatcccett  1800
cagtatggtg gttctcaact tgttcatcgt gtgaaaacct acagaaagat agcaccatgg   1860
acccagcact ccaaagacat catgcaaacc ctgtctagat attacagcaa tgctttttca   1920
gatgccgata gacaagattc cattaatctc ttcctgggag ttttccatcc cactgaaggg   1980
aaacctcatc tctgggagct cccaacagat ttttatttgc atcacaaaaa taccatgaga   2040
cttttgccaa caagaagaag ttatacttac tggtggacac cagaggtgat aaagcattta   2100
ccattgccct atgatgaagt tatctgtgct gtgaacttaa agaagttgat agtgaagaaa   2160
ttccacaaat atgaagaaga gattgatatc cacaatgagt tctttcggcc atatgagttg   2220
agcagctttg atgatacctt ttgcttggct atgacaagct cagcacgtga ctttatgcct   2280
aagaccgttg gaattgatcc aagtccattt actgtgcgta aaccagatga aactggaaaa   2340
```

-continued

```
tcagtattgg gaaacaaaag caatagagaa gaagctgtat tacagcggaa aacggcagcc    2400
agcgccccgc cgccccccag cgaggaggct gtgtccagca gctctgagga tgactctggg    2460
actgatcggg aagaagaggg ctctgtgtct cagcgctcca ctcccgtgaa gatgactgat    2520
gcaggagaca gtgccaaagt gaccgagaat gtggtccaac ccatgaagga gctatatgga    2580
attaacctct cagatggcct ctcagaagaa gatttctcca tttattcaag atttgttcag    2640
ctggggcaga gtcaacataa acaagacaag aatagccagc agccctgttc taggtgctca    2700
gatggagtta taaaactaac acccatctcg gctttctcgc aagataacat ctatgaagtt    2760
cagcccccaa gagtagacag aaaatctaca gagatcttcc aagcccacat ccaggccagc    2820
caaggtatca tgcagcccct aggaaaagag gactcctcca tgtaccgaga gtacatcagg    2880
aaccgctacc tgtgaaaaga gcgcaggtcc acctggtgga cacgtctgat tagcttagaa    2940
cctgtcttgt ctcatcttca aaaggtaact tattaaaagt cctttgcgtc tgaagccttt    3000
ctccttttct gtcacttgca aattccaaat tatagctaat aaagatgact agataatttg    3060
c                                                                   3061
```

```
<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
aatgcaaccg tgacacaagt acac                                            24

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
cgtatgaatt gagtagtttt gatg                                            24

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
gctgggggag gggagactac acag                                            24

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atggacttgg atcaatgcca acag                                            24

<210> SEQ ID NO 6
<211> LENGTH: 24
<212> TYPE: DNA
```

```
<213> ORGANISM: Artificial Sequence
<220> FEATURE:
<223> OTHER INFORMATION: Synthetic

<400> SEQUENCE: 6
ccaccacatc aacaggctca cagg                                              24

<210> SEQ ID NO 7
<211> LENGTH: 12
<212> TYPE: DNA
<213> ORGANISM: Homo sapiens
<220> FEATURE:
<221> NAME/KEY: misc_feature
<222> LOCATION: (8)..(8)
<223> OTHER INFORMATION: n is a, c, g, or t

<400> SEQUENCE: 7
ttgaagantg at                                                           12

<210> SEQ ID NO 8
<211> LENGTH: 12
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t

<400> SEQUENCE: 8
gtcttgngaa tg                                                           12

<210> SEQ ID NO 9
<211> LENGTH: 22
<212> TYPE: PRT
<213> ORGANISM: Homo sapiens

<400> SEQUENCE: 9

Phe Leu Val Gly Ser Asn Asn Ala Glu Thr Lys Tyr Arg Val Leu Lys
1               5                   10                  15

Ile Asp Arg Thr Glu Pro
            20

<210> SEQ ID NO 10
<211> LENGTH: 9
<212> TYPE: PRT
<213> ORGANISM: Drosophila melanogaster

<400> SEQUENCE: 10

Tyr Arg Arg Phe Leu Thr Leu Ala His
1               5

<210> SEQ ID NO 11
<211> LENGTH: 13
<212> TYPE: PRT
<213> ORGANISM: Caenorhabditis elegans

<400> SEQUENCE: 11

Tyr Ile Ile Cys Asp Ser Thr Gly Ser Arg Asn Ile Asp
1               5                   10

<210> SEQ ID NO 12
<211> LENGTH: 10
<212> TYPE: PRT
```

```
<213> ORGANISM: Saccharomyces cerevisiae

<400> SEQUENCE: 12

Tyr Ile Lys Arg Met Phe Ile Glu Leu Val
1               5                   10
```

FIG4 GENE MUTATIONS IN NEURODEGENERATION

This invention was made with government support under grant number GM24872 awarded by the National Institutes of Health. The government has certain rights in the invention.

FIELD OF THE INVENTION

The present invention relates to neuropathy, in particular to mutations in the FIG4 gene. The present invention also provides assays for the detection of variant FIG4 alleles, and assays for detecting FIG4 polymorphisms and mutations associated with disease states.

BACKGROUND OF THE INVENTION

Charcot-Marie-Tooth disease (CMT) is one of the most common inherited neurological disorders, affecting approximately 1 in 2,500 people in the United States. The disease is named for the three physicians who first identified it in 1886—Jean-Martin Charcot and Pierre Marie in Paris, France, and Howard Henry Tooth in Cambridge, England. CMT, also known as hereditary motor and sensory neuropathy (HMSN) or peroneal muscular atrophy, comprises a group of disorders that affect peripheral nerves. The peripheral nerves lie outside the brain and spinal cord and supply the muscles and sensory organs in the limbs as well as providing proprioceptive input from the periphery to the brain. Disorders that affect the peripheral nerves are called peripheral neuropathies.

The neuropathy of CMT affects both motor and sensory nerves. A typical feature includes weakness of the foot and lower leg muscles, which may result in foot drop and a high-step page gait with frequent tripping or falls. Foot deformities, such as high arches and hammertoes (a condition in which the middle joint of a toe bends upwards) are also characteristic due to weakness of the small muscles in the feet. In addition, the lower legs may take on an "inverted champagne bottle" appearance due to the loss of muscle bulk. Later in the disease, weakness and muscle atrophy may occur in the hands, resulting in difficulty with fine motor skills. In CMT there is a distal muscle wasting and weakness reflecting a nerve length dependent process.

Onset of symptoms is most often in adolescence or early adulthood, however presentation may be delayed until mid-adulthood. The severity of symptoms is quite variable in different patients and even among family members with the disease. Progression of symptoms is gradual. Pain can range from mild to severe, and some patients may need to rely on foot or leg braces or other orthopedic devices to maintain mobility. Although in rare cases patients may have respiratory muscle weakness, CMT is not considered a fatal disease and people with most forms of CMT have a normal life expectancy.

There is no cure for CMT, but physical therapy, occupational therapy, braces and other orthopedic devices, and even orthopedic surgery can help patients cope with the disabling symptoms of the disease. In addition, pain-killing drugs can be prescribed for patients who have severe pain.

Physical and occupational therapy, the preferred treatment for CMT, involves muscle strength training, muscle and ligament stretching, stamina training, and moderate aerobic exercise. Most therapists recommend a specialized treatment program designed with the approval of the patient's physician to fit individual abilities and needs. Therapists also suggest entering into a treatment program early; muscle strengthening may delay or reduce muscle atrophy, so strength training is most useful if it begins before nerve degeneration and muscle weakness progress to the point of disability.

Stretching may prevent or reduce joint deformities that result from uneven muscle pull on bones. Exercises to help build stamina or increase endurance will help prevent the fatigue that results from performing everyday activities that require strength and mobility. Moderate aerobic activity can help to maintain cardiovascular fitness and overall health. Most therapists recommend low-impact or no-impact exercises, such as biking or swimming, rather than activities such as walking or jogging, which may put stress on fragile muscles and joints.

Many CMT patients require ankle braces and other orthopedic devices to maintain everyday mobility and prevent injury Ankle braces can help prevent ankle sprains by providing support and stability during activities such as walking or climbing stairs. High-top shoes or boots can also give the patient support for weak ankles Thumb splints can help with hand weakness and loss of fine motor skills. Assistive devices should be used before disability sets in because the devices may prevent muscle strain and reduce muscle weakening. Some CMT patients may decide to have orthopedic surgery to reverse foot and joint deformities.

CMT is one cause of peripheral neuropathy. It is desired to make a specific diagnosis since different causes of peripheral neuropathy are managed with diagnostic specific therapeutic approaches.

Clearly there is a great need for characterization of the poorly understood molecular basis of CMT as well as for improved diagnostics and treatments for CMT.

SUMMARY OF THE INVENTION

The present invention relates to neuropathy, in particular to mutations in the FIG4 gene. The present invention also provides assays for the detection of variant FIG4 alleles, and assays for detecting FIG4 polymorphisms and mutations associated with disease states. For example, in some embodiments, the present invention provides a method for detection of a variant FIG4 gene in a subject, comprising: detecting the presence or absence of a variant FIG4 gene in a biological sample from the subject. In some embodiments, the variant FIG4 gene encodes a variant FIG4 polypeptide (e.g., a F98fsX102 truncation mutant in exon 4 of FIG4, a I41T mutation in exon 2 of FIG4, a R183X mutation in exon 6 of FIG4, combinations of two or more of the aforementioned mutations, or functionally equivalent mutations, truncations, etc). In some embodiments, the FIG4 allele comprises a heterozygous mutation that causes truncation of the FIG4 protein or a truncation mutation as a compound heterozygote with the I41T mutation or another missense mutation. In some embodiments, the subject exhibits symptoms of neuropathy (e.g., Charcot Marie Tooth type 4J neuropathy (CMT4J), an autosomal recessive neuropathy or Dejerine-Sottas neuropathy). In some embodiments, the biological sample is a blood sample, a serum sample, a plasma sample, a tissue sample, a urine sample, a DNA sample, or an amniotic fluid sample although the invention is not limited to these sample types. In some embodiments, the subject is an embryo, a fetus, a newborn animal, or a young animal. In some embodiments, the animal is a human. In some embodiments, detecting the presence of a variant FIG4 gene comprises performing a nucleic acid hybridization assay or other nucleic acid analysis technique. In some embodiments, the detecting the presence of a variant FIG4 gene comprises an immunoassay or other protein analysis technique.

In some embodiments, the present invention provides a method for detection of a variant FIG4 gene in a subject, wherein the variant FIG4 gene comprises any combination of compound heterozygous or homozygous mutant alleles of FIG4, comprising: detecting the presence or absence of the variant FIG4 gene in a biological sample from the subject.

Embodiments of the present invention further provide a method, comprising: contacting an animal exhibiting symptoms of CMT4J disease with a test compound; and determining the presence or absence of reduced symptoms in the presence of the test compound relative to the absence of the test compound. In some embodiments, the animal expresses a variant FIG4 polypeptide (e.g., a F98fsX102 truncation mutant in exon 4 of FIG4, a I41T mutation in exon 2 of FIG4, a R183X mutation in exon 6 of FIG4, or a combination of two or more of the aforementioned mutations).

The present invention additionally provides a method, comprising: contacting an isolated cell expressing a variant FIG4 polypeptide with a test compound; and assaying the activation of Fab1/PIKfyve in the cell in the presence of the test compound relative to the level in the absence of the test compound. In some embodiments, the variant FIG4 polypeptide comprises a F98fsX102 truncation mutant in exon 4 of FIG4, a I41T mutation in exon 2 of FIG4, a R183X mutation in exon 6 of FIG4, or a combination of two or more of the aforementioned mutations.

DESCRIPTION OF THE FIGURES

FIG. 13 shows the cDNA sequence of FIG4 (SEQ ID NO:1). First codon (ATG) is underlined. The site of I41 T mutation is underlined—T to C nucleotide change in the mutant allele.

DEFINITIONS

To facilitate understanding of the invention, a number of terms are defined below.

Figure 4:
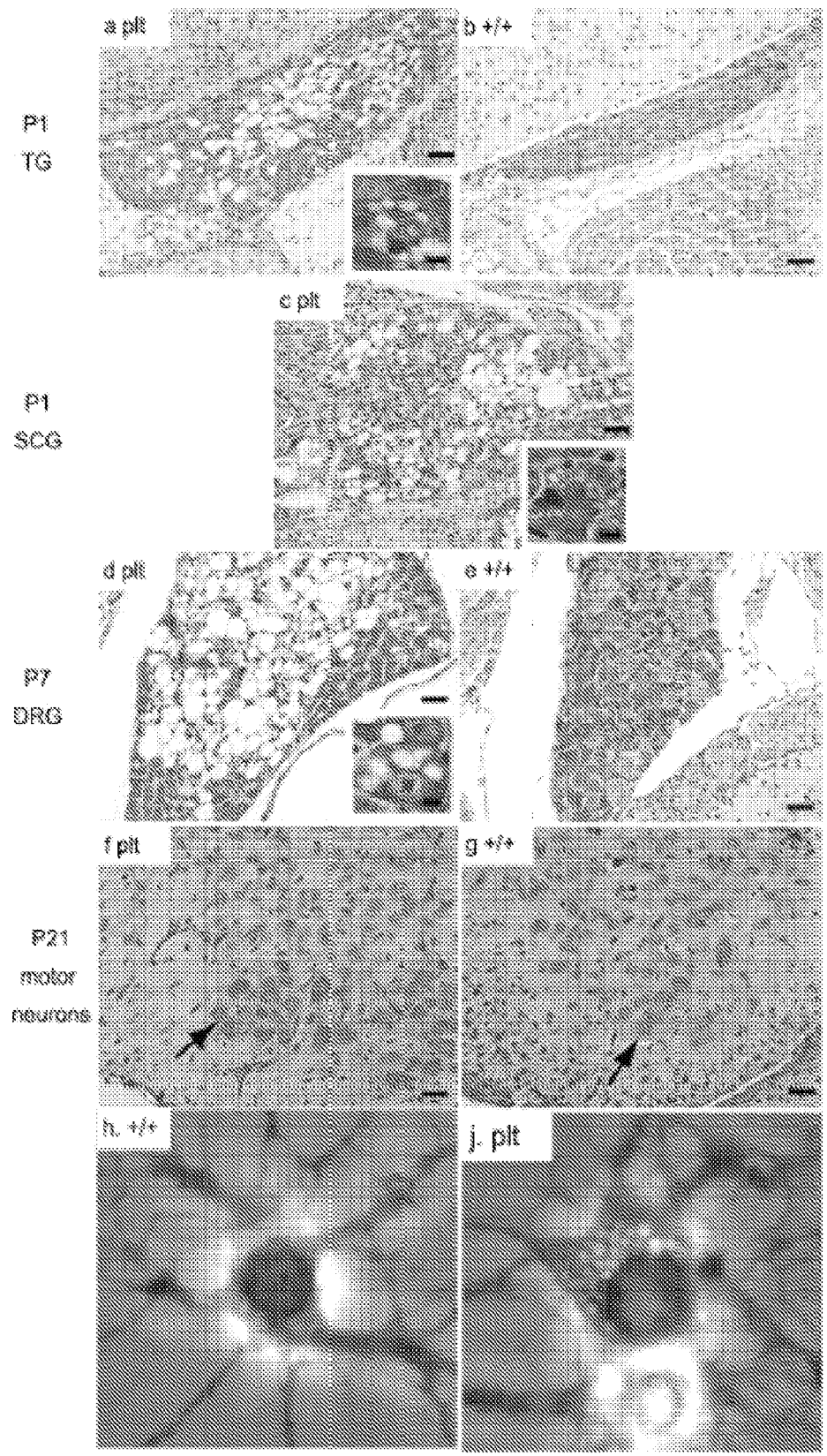
FIG. 4 shows neuropathology in pale tremor mice. a-b, Trigeminal ganglia at P1 (postnatal day 1). c, Superior cervical ganglion at P1. d-e, Dorsal root ganglia from lumbar region at P7. Insets (a,c,d) demonstrate accumulation of cytoplasmic vacuoles. f-g, Spinal cord ventral horn at P21. Motor neuron cell bodies, arrows. h-i Cultured hippocampal neurons from E16.5 embryos. TG, trigeminal ganglia. SCG, superior cervical ganglia. DRG, dorsal root ganglia. Scale bar: 25 microns for panels, 12.5 microns for insets (ag).
Figure 12:
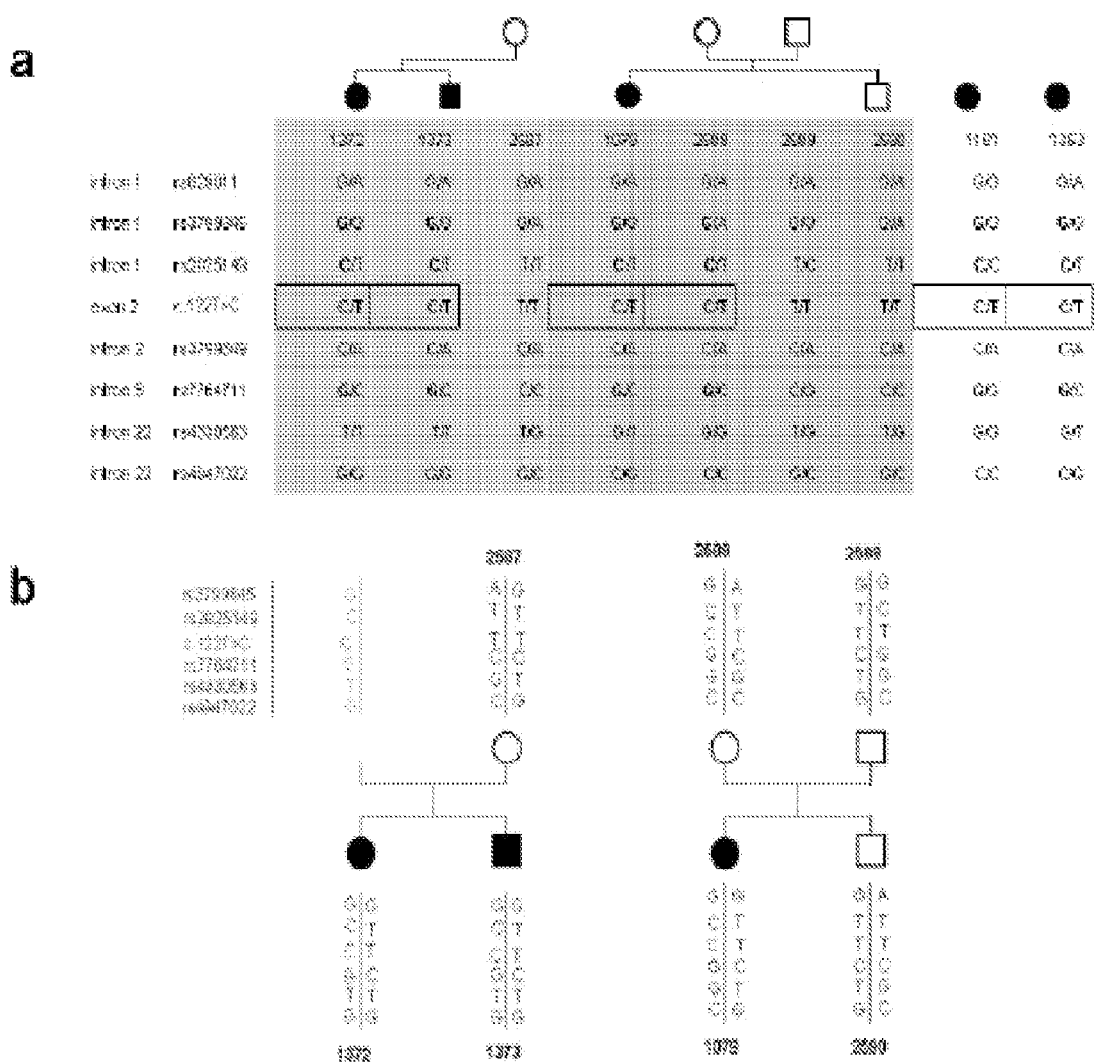
FIG. 12 shows haplotypes of CMT patients with mutations in FIG4. a. Genotypes. Seven SNPs from the HapMap database, and the Ile41Thr mutation (c.122T>C) were genotyped for patients and family members. b. Haplotypes. The five SNPs shown in black were informative in the two available pedigrees and permitted reconstruction of the haplotypes. The Ile41Thr (c.122T>C) allele is carried by the same haplotype in all four patients. The Ile41Thr allele has a calculated LD coefficient D' equal to 1 for rs3799845, rs2025149 and rs7764711. D' equals 0.11 for rs4330563 and rs4947022.

As used herein, the term "FIG4" when used in reference to a protein or nucleic acid refers to a FIG4 protein or FIG4 nucleic acid encoding a protein that, in some mutant forms, is correlated with CMT (e.g., CMT type 4J). The term FIG4 encompasses both proteins that are identical to wild-type FIG4 and those that are derived from wild type FIG4 (e.g., variants of FIG4 or chimeric genes constructed with portions of FIG4 coding regions). In some embodiments, the "FIG4" is the wild type FIG4 nucleic acid or FIG4 amino acid sequence. The cDNA sequence of FIG4 is shown in FIG. 12 (SEQ ID NO:1).

As used herein, the term "instructions for using said kit for said detecting the presence or absence of a variant FIG4 polypeptide in a said biological sample" includes instructions for using the reagents contained in the kit for the detection of variant and wild type FIG4 nucleic acids or polypeptides. In some embodiments, the instructions further comprise the statement of intended use required by the U.S. Food and Drug Administration (FDA) in labeling in vitro diagnostic products.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain by virtue of the well established genetic code. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency or an oligonucleotide and/or mRNA based microarray. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.). Furthermore, when used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in *Nucleic Acid Hybridization* (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42 C when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.5% SDS, 5× Denhardt's reagent and 100 μg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42 C in a solution consisting of 5×SSPE (43.8 g/l NaCl, 6.9 g/l NaH$_2$PO$_4$H$_2$O and 1.85 g/l EDTA, pH adjusted to 7.4 with NaOH), 0.1% SDS, 5× Denhardt's reagent (50× Denhardt's contains per 500 ml: 5 g Ficoll (Type 400, Pharamcia), 5 g BSA (Fraction V; Sigma)) and 100 μg/ml denatured salmon sperm DNA followed by washing in a solution comprising 5×SSPE, 0.1% SDS at 42 C when a probe of about 500 nucleotides in length is employed. The present invention is not limited to the hybridization of probes of about 500 nucleotides in length. The present invention contemplates the use of probes between approximately 10 nucleotides up to several thousand (e.g., at least 5000) nucleotides in length.

One skilled in the relevant art understands that stringency conditions may be altered for probes of other sizes (See e.g., Anderson and Young, Quantitative Filter Hybridization, in *Nucleic Acid Hybridization* (1985) and Sambrook et al., Molecular Cloning: A Laboratory Manual, Cold Spring Harbor Press, NY (1989)).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, *Adv. Appl. Math.* 2: 482 (1981)) by the homology alignment algorithm of Needleman and Wunsch (Needleman and Wunsch, *J. Mol. Biol.* 48:443 (1970)), by the search for similarity method of Pearson and Lipman (Pearson and Lipman, *Proc. Natl. Acad. Sci.* (*U.S.A.*) 85:2444 (1988)), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., FIG4).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., the FIG4 gene).

As used herein, the term "detection assay" refers to an assay for detecting the presence or absence of variant nucleic acid sequences (e.g., polymorphism or mutations) in a given allele of a particular gene (e.g., the FIG4 gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid by virtue of sequence specific complementarity. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 (1972)). Other nucleic acid will not be replicated by this amplification enzyme. Similarly, in the case of T7 RNA polymerase, this amplification enzyme has a stringent specificity for its own promoters (Chamberlin et al., Nature 228:227 (1970)). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press (1989)).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding FIG4 includes, by way of example, such nucleic acid in cells ordinarily expressing FIG4 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, FIG4 antibodies are purified by removal of contaminating non-immunoglobulin proteins; they are also purified by the removal of immunoglobulin that does not bind FIG4. The removal of non-immunoglobulin proteins and/or the removal of immunoglobulins that do not bind FIG4 results in an increase in the percent of FIG4-reactive immunoglobulins in the sample. In another example, recombinant FIG4polypeptides are expressed in bacterial host cells and the polypeptides are purified by the removal of host cell proteins; the percent of recombinant FIG4polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 (1989)).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 (1989)).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the FIG4 mRNA-specific signal observed on Northern blots). The amount of mRNA present in the band corresponding in size to the correctly spliced FIG4transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product). As used herein, the term "reporter gene" refers to a gene encoding a protein that may be assayed. Examples of reporter genes include, but are not limited to, luciferase (See, e.g., deWet et al., *Mol. Cell. Biol.* 7:725 (1987) and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the term "entering" as in "entering said genetic variation information into said computer" refers to transferring information to a "computer readable medium." Information may be transferred by any suitable method, including but not limited to, manually (e.g., by typing into a computer) or automated (e.g., transferred from another "computer readable medium" via a "processor").

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "computer implemented method" refers to a method utilizing a "CPU" and "computer readable medium."

DETAILED DESCRIPTION OF THE INVENTION

The present invention relates to neuropathy, in particular to mutations in the FIG4 gene. The present invention also provides assays for the detection of variant FIG4 alleles, and assays for detecting FIG4 polymorphisms and mutations associated with disease states.

Certain exemplary embodiments of the invention are described below. The invention is not limited to those embodiments described herein. One skilled in the art recognizes that other embodiments are within the scope of the present invention.

I. Diagnostic Applications

In some embodiments, the present invention provides methods of diagnosing CMT4J disease based on the presence or absence of variant alleles of FIG4.

A. FIG4 Alleles

As described below, experiments conducted during the course of development of some embodiments of the present invention resulted in the identification of variant FIG4 alleles associated with CMT disease type 4J. Accordingly, in some embodiments the present invention provides FIG4 mutant alleles that are associated with diseases states. Exemplary FIG4 mutant alleles include, but are not limited to, those that encode F98fsX102 in exon 4, I41T in exon 2 and R183X in exon 6. In some embodiments, individuals affected with CMT4J carry both the I41T and one of the other mutations. In some embodiments, affected individuals are compound heterozygotes. In some embodiments, effected individuals have any FIG4 mutation that cause truncation of the FIG4 protein, present as a homozygous condition. In other embodiments, affected individuals have a mutation that causes a truncation of FIG4 as a compound heterozygote with the I41T mutation or another missense mutation.

In other embodiments of the present invention, additional alleles of FIG4 are provided. In preferred embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In other embodiments of the present invention, variants of the disclosed FIG4 sequences are provided. In preferred embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

In other embodiments, the present invention provides FIG4 polynucleotide sequences that encode FIG4 polypeptide sequences. Other embodiments of the present invention provide fragments, fusion proteins or functional equivalents of these FIG4 proteins. In still other embodiment of the present invention, nucleic acid sequences corresponding to FIG4 variants, homologs, and mutants may be used to generate recombinant DNA molecules that direct the expression of the FIG4 variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture).

In some embodiments, depending upon the host employed in a recombinant production procedure, the polypeptide of the present invention may be glycosylated or may be non-glycosylated. In other embodiments, the polypeptides of the invention may also include an initial methionine amino acid residue.

B. Detection of FIG4 Alleles

In some embodiments, the present invention provides methods of detecting the presence of wild type or variant (e.g., mutant or polymorphic) FIG4 nucleic acids or polypeptides. The detection of mutant FIG4 finds use in the diagnosis of disease (e.g., CMT4J).

Accordingly, the present invention provides methods for determining whether a patient has an increased susceptibility to CMT4J by determining whether the individual has a variant FIG4 allele. In other embodiments, the present invention provides methods for determining an increased risk for CMT4J to an individual based on the presence or absence of one or more variant alleles of FIG4 (e.g., those described herein). In some embodiments, the variation causes a truncation of the FIG4 protein.

A number of methods are available for analysis of variant (e.g., mutant or polymorphic) nucleic acid sequences. Assays for detecting variants (e.g., polymorphisms or mutations) fall into several categories, including, but not limited to direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following assays are useful in the present invention.

A. Sample

Any patient sample containing FIG4 nucleic acids or polypeptides may be tested according to the methods of the present invention. By way of non-limiting examples, the sample may be tissue, blood, urine, semen, or a fraction thereof (e.g., plasma, serum, urine supernatant, urine cell pellet or prostate cells).

The patient sample may undergo preliminary processing designed to isolate or enrich the sample for the FIG4 nucleic acids or polypeptides or cells that contain FIG4. A variety of techniques known to those of ordinary skill in the art may be used for this purpose, including but not limited: centrifugation; immunocapture; cell lysis; and, nucleic acid target capture (See, e.g., EP Pat. No. 1 409 727, herein incorporated by reference in its entirety).

B. DNA and RNA Detection

The FIG4 variants of the present invention may be detected as genomic DNA or mRNA using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, fluorescent or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2. Microarrays

In some embodiments, microarrays are utilized for detection of FIG4 nucleic acid sequences. Examples of microarrays include, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink jet printing; or, electrochemistry on microelectrode arrays.

Arrays can also be used to detect copy number variations at al specific locus. These genomic microarrays detect microscopic deletions or other variants that lead to disease causing alleles.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

FIG4 nucleic acid may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800, 159; Mullis et al., Meth. Enzymol. 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Qβ replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

4. Detection Methods

Non-amplified or amplified FIG4 nucleic acids can be detected by any conventional means. For example, nucleic acid can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

C. Detection of Variant FIG4 Proteins

In other embodiments, variant FIG4 polypeptides are detected (e.g., including, but not limited to, those described in Example 1). Any suitable method may be used to detect truncated or mutant FIG4 polypeptides including, but not limited to, those described below.

1. Cell Free Translation

For example, in some embodiments, cell-free translation methods from Ambergen, Inc. (Boston, Mass.) are utilized. Ambergen, Inc. has developed a method for the labeling, detection, quantitation, analysis and isolation of nascent proteins produced in a cell-free or cellular translation system without the use of radioactive amino acids or other radioactive labels. Markers are aminoacylated to tRNA molecules. Potential markers include native amino acids, non-native amino acids, amino acid analogs or derivatives, or chemical moieties. These markers are introduced into nascent proteins from the resulting misaminoacylated tRNAs during the translation process.

One application of Ambergen's protein labeling technology is the gel free truncation test (GFTT) assay (See e.g., U.S. Pat. No. 6,303,337, herein incorporated by reference). In some embodiments, this assay is used to screen for truncation mutations in a FIG4 protein. In the GFTT assay, a marker (e.g., a fluorophore) is introduced to the nascent protein during translation near the N-terminus of the protein. A second and different marker (e.g., a fluorophore with a different emission wavelength) is introduced to the nascent protein near the C-terminus of the protein. The protein is then separated from the translation system and the signal from the markers is measured. A comparison of the measurements from the N and C terminal signals provides information on the fraction of the molecules with C-terminal truncation (i.e., if the normalized signal from the C-terminal marker is 50% of the signal from the N-terminal marker, 50% of the molecules have a C-terminal truncation).

2. Antibody Binding

In still further embodiments of the present invention, antibodies (See below for antibody production) are used to determine if an individual contains an allele encoding a variant FIG4 polypeptide. In preferred embodiments, antibodies are utilized that discriminate between variant (i.e., truncated proteins); and wild-type proteins. In some particularly preferred embodiments, the antibodies are directed to the C-terminus of FIG4 proteins. Proteins that are recognized by the N-terminal, but not the C-terminal antibody are truncated. In some embodiments, quantitative immunoassays are used to determine the ratios of C-terminal to N-terminal antibody binding. In other embodiments, identification of variants of FIG4 is accomplished through the use of antibodies that differentially bind to wild type or variant forms of FIG4 proteins.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981, 785, 6,159,750, and 5,358,691, each of which is herein incorporated by reference. In some embodiments, the analysis and presentation of results is also automated. For example, in some embodiments, software that generates a prognosis based on the result of the immunoassay is utilized. In other embodiments, the immunoassay described in U.S. Pat. Nos. 5,599,677 and 5,672,480; each of which is herein incorporated by reference.

C. Kits for Analyzing Risk of FIG4 Diseases

The present invention also provides kits for determining whether an individual contains a wild-type or variant (e.g., mutant or polymorphic) allele of FIG4. In some embodiments, the kits are useful for determining whether the subject is at risk of developing CMT4J. The diagnostic kits are produced in a variety of ways. In some embodiments, the kits contain at least one reagent useful, necessary, or sufficient for specifically detecting a mutant FIG4 allele or protein. In preferred embodiments, the kits contain reagents for detecting a truncation in the FIG4 polypeptide. In preferred embodiments, the reagent is a nucleic acid that hybridizes to nucleic acids containing the mutation and that does not bind to nucleic acids that do not contain the mutation. In other preferred embodiments, the reagents are primers for amplifying the region of DNA containing the mutation. In still other embodiments, the reagents are antibodies that preferentially bind either the wild-type or truncated or variant FIG4 proteins.

In some embodiments, the kit contains instructions for determining whether the subject is at risk for developing CMT4J disease. In preferred embodiments, the instructions specify that risk for developing CMT4J disease is determined by detecting the presence or absence of a mutant FIG4 allele in the subject, wherein subjects having an mutant allele are at greater risk for FIG4 disease.

The presence or absence of a disease-associated mutation in a FIG4 gene can be used to make therapeutic or other medical decisions. For example, couples with a family history of CMT4J disease may choose to conceive a child via in vitro fertilization and pre-implantation genetic screening. In this case, fertilized embryos are screened for mutant (e.g., disease associated) alleles of the FIG4 gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a FIG4 allele known to be associated with CMT4J disease allows for early intervention.

In some embodiments, the kits include ancillary reagents such as buffering agents, nucleic acid stabilizing reagents, protein stabilizing reagents, and signal producing systems (e.g., florescence generating systems as Fret systems), and software (e.g., data analysis software). The test kit may be packages in any suitable manner, typically with the elements in a single container or various containers as necessary along with a sheet of instructions for carrying out the test. In some embodiments, the kits also preferably include a positive control sample.

D. Bioinformatics

For example, in some embodiments, a computer-based analysis program is used to translate the raw data generated by the detection assay (e.g., the presence, absence, or amount of a given FIG4 allele or polypeptide) into data of predictive value for a clinician. The clinician can access the predictive data using any suitable means. Thus, in some preferred embodiments, the present invention provides the further benefit that the clinician, who may not be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant FIG4), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing CMT4J or a diagnosis of CMT4J) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

IV. Generation of FIG4 Antibodies

The present invention provides isolated antibodies or antibody fragments (e.g., FAB fragments). Antibodies can be generated to allow for the detection of an FIG4 protein. The antibodies may be prepared using various immunogens. In one embodiment, the immunogen is a human FIG4 peptide to generate antibodies that recognize a human FIG4 protein. Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against FIG4. For the production of antibody, various host animals can be immunized by injection with the peptide corresponding to the FIG4 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward FIG4, it is contemplated that any technique that provides for the production of antibody molecules by continuous cell lines in culture will find use with the present invention (See e.g., Harlow and Lane, *Antibodies: A Laboratory Manual*, Cold Spring Harbor Laboratory Press, Cold Spring Harbor, N.Y.). These include but are not limited to the hybridoma technique originally developed by Köhler and Milstein (Köhler and Milstein, Nature 256:495-497 (1975)), as well as the trioma technique, the human B-cell hybridoma technique (See e.g., Kozbor et al., Immunol. Tod., 4:72 (1983)), and the EBV-hybridoma technique to produce human monoclonal antibodies (Cole et al.,in *Monoclonal Antibodies and Cancer Therapy*, Alan R. Liss, Inc., pp. 77-96 (1985)).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 (1983)) or by transforming human B cells with EBV virus in vitro (Cole et al., in *Monoclonal Antibodies and Cancer Therapy*, Alan R. Liss, pp. 77-96 (1985)).

In addition, it is contemplated that techniques described for the production of single chain antibodies (U.S. Pat. No. 4,946,778; herein incorporated by reference) will find use in producing FIG4 specific single chain antibodies. An additional embodiment of the invention utilizes the techniques described for the construction of Fab expression libraries (Huse et al., Science 246:1275-1281 (1989)) to allow rapid and easy identification of monoclonal Fab fragments with the desired specificity for FIG4.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')$_2$ fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

Additionally, using the above methods, antibodies can be generated that recognize the variant forms of FIG4 proteins, while not recognizing the wild type forms of the FIG4 proteins.

The foregoing antibodies can be used in methods known in the art relating to the localization and structure of FIG4 proteins (e.g., for Western blotting, immunoprecipitaion and immunocytochemistry), measuring levels thereof in appropriate biological samples, etc. The antibodies can be used to detect FIG4 protein in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of human FIG4 proteins using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of FIG4 detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of FIG4 or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of FIG4. Such antibodies can also be used diagnostically to measure abnormal expression of FIG4 proteins, or the aberrant formation of protein complexes, which may be indicative of a disease state.

V. Gene Therapy Using FIG4

The present invention also provides methods and compositions suitable for gene therapy to alter FIG4 protein expression, production, or function. As described above, the present invention provides human FIG4 genes and provides methods of obtaining FIG4 genes from other species. Thus, the methods described below are generally applicable across many species. In some embodiments, it is contemplated that the gene therapy is performed by providing a subject with a wild-type allele of FIG4 (i.e., an allele that does not contain a FIG4 disease causing mutation). Subjects in need of such therapy are identified by the methods described above.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 (1992)). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 (1991)), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 (1992); See also, La Salle et al., Science 259:988-990 (1993)); and a defective adeno-associated virus vector (Samulski et al., J. Virol., 61:3096-3101 (1987); Samulski et al., J. Virol., 63:3822-3828 (1989); and Lebkowski et al., Mol. Cell. Biol., 8:3988-3996 (1988)).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 (1992); Wu and Wu, J. Biol. Chem., 263:14621 (1988); and Williams et al., Proc. Natl. Acad. Sci. USA 88:2726 (1991)). Receptor-mediated DNA delivery approaches can also be used (Curiel et al., Hum. Gene Ther., 3:147 (1992); and Wu and Wu, J. Biol. Chem., 262:4429 (1987)).

VI. Transgenic Animals Expressing Exogenous FIG4 Genes and Homologs, Mutants, and Variants Thereof The present invention contemplates the generation of transgenic animals comprising an exogenous FIG4 gene or homologs, mutants, or variants thereof. In preferred embodiments, the transgenic animal displays an altered phenotype as compared to wild-type animals. In some embodiments, the altered phenotype is the overexpression of mRNA for a FIG4 gene as compared to wild-type levels of FIG4 expression. In other embodiments, the altered phenotype is the decreased expression of mRNA for an endogenous FIG4 gene as compared to wild-type levels of endogenous FIG4 expression. In some preferred embodiments, the transgenic animals comprise mutant (e.g., truncated) alleles of FIG4. Methods for analyzing the presence or absence of such phenotypes include Northern blotting, mRNA protection assays, and RT-PCR. In other embodiments, the transgenic mice have a knock out mutation of the FIG4 gene. In preferred embodiments, the transgenic animals display a CMT4J disease phenotype.

Such animals find use in research applications (e.g., identifying signaling pathways involved in CMT4J), as well as drug screening applications (e.g., to screen for drugs that prevents CMT4J disease. For example, in some embodiments, test compounds (e.g., a drug that is suspected of being useful to treat CMT4J disease) and control compounds (e.g., a placebo) are administered to the transgenic animals and the control animals and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 (1985)). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 (1976)). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. (1986)). The viral vector system used to introduce the transgene is typically a replication-defective retrovirus carrying the transgene (Jahner et al., Proc. Natl. Acad. Sci. USA 82:6927 (1985)). Transfection is easily and efficiently obtained by culturing the blastomeres on a monolayer of virus-producing cells (Van der Putten, supra; Stewart, et al., EMBO J., 6:383 (1987)). Alternatively, infection can be performed at a later stage. Virus or virus-producing cells can be injected into the blastocoele (Jahner et al., Nature 298:623 (1982)). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra (1982)). Additional means of using retroviruses or retroviral vectors to create transgenic animals known to the art involves the micro-injection of retroviral particles or mitomycin C-treated cells producing retrovirus into the perivitelline space of fertilized eggs or early embryos (PCT International Application WO 90/08832 (1990), and Haskell and Bowen, Mol. Reprod. Dev., 40:386 (1995)).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 (1981); Bradley et al., Nature 309:255 (1984); Gossler et al., Proc. Acad. Sci. USA 83:9065 (1986); and Robertson et al., Nature 322:445

(1986)). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 (1988)). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants. Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

A. Methods

Animals. The plt mutation arose on a mixed strain background derived from crosses between the 4 inbred strains 129/Ola, C57BL/6J, C3H, and SJL (Adamska et al., Dev Dyn 233, 368-72 (2005)). For genetic mapping, plt/+ heterozygotes were crossed with strain CAST/Ei (Jackson Laboratory, Bar Harbor, Me.). Animals were housed and cared for in accordance with NIH guidelines.

Genotyping and Markers. Genotyping was carried out using microsatellite markers from public databases as well as novel microsatellite markers designed from mouse genomic sequence. D10Umi13 was amplified with the forward primer 5'-CCACC ACATC AACAG GCTCA CAGG (SEQ ID NO:1) and reverse primer 5'-AATGC AACCG TGACA CAAGT ACAC (SEQ ID NO:2). PCR was carried out with the PCR core kit (Qiagen). PCR products were separated on 6% acrylamide gels and stained with ethidium bromide. The plt mutation was genotyped by PCR with a forward primer in intron 18 (5'CGTAT GAATT GAGTA GTTTT GATG; SEQ ID NO: 3) and two reverse primers, one in the proximal LTR of the inserted Etn2β element (5' GCTGG GGGAG GGGAG ACTAC ACAG; SEQ ID NO:4) and one in exon 19 (5' ATGGA CTTGG ATCAA TGCCA ACAG; SEQ ID NO:5) RT-PCR. Total RNA was isolated from brain of P7 mice, prior to extensive neurodegeneration. cDNA was synthesized using the First Strand cDNA Synthesis Kit (Invitrogen Corp.). RT-PCR was carried out with the PCR Core Kit (Qiagen). Long range PCR was performed with the Expand Long Template PCR System (Roche).

Sequencing. Mouse and human PCR products were gel-purified. Automated sequencing was carried out by the University of Michigan DNA Sequencing Core and at the Baylor College of Medicine.

Northern blot: The Northern blot with 3 ug of polyA+ RNA was prepared as previously described (Kohrman et al., J Biol Chem 271, 17576-81 (1996)). The hybridization probe, a 1 kb RT-PCR product containing exons 8 to 15, was labeled with two radiolabeled nucleotide triphosphates.

Histology. Tissues were sectioned and stained at HistoSery (Germantown, Md.). Fast blue/eosin staining was carried out in the Department of Pathology, University of Michigan. Light microscopy was performed on an Olympus BX-51 microscope and DP50 camera. Sciatic and femoral nerves were sectioned and stained with osmium for electron microscopy at the Microscopy and Image Analysis Laboratory, University of Michigan and visualized on a Phillips CM-100 microscope. Skin whole mounts were prepared from P10 mice with the guidance of Dr. Andrzej Dlugosz, Department of Dermatology, University of Michigan. The commercial depilatory Nair was applied to the dorsal surface for five minutes followed by washing with warm water to remove hair. The skin was dissected and superficial fascia removed. Follicles were visualized on a standard dissecting microscope with transmitted light.

Neurophysiology. Nerve conduction velocities were recorded from affected pale tremor mice and littermate controls. Mice were anesthetized with ketamine/zylazine and placed under a heating lamp to maintain body temperature at 32° C. Recordings were obtained using a Nicolet VikingQuest portable system and Nicolet disposable EEG needles. Tail sensory responses were obtained by stimulating proximally over a 3 cm region. Sciatic nerve motor velocities were obtained by stimulating distally at the sciatic notch and proximally at the knee.

Cell culture and immunoflourescence. Primary fibroblasts were cultured from mouse tail biopsies treated with collagenase. Cells were plated in Dulbecco's modified Eagle medium (DMEM) with 10% fetal bovine serum (FBS) and maintained at 37° C. with 5% $CO_2$ for up to 3 passages. For immunoflourescence, 100,000 cells were seeded on lysine-coated cover slips in 35 mm dishes. For labeling with rat anti-LAMP2 (ABL-93, U. Iowa Hybridoma Bank) cells were fixed with ice cold methanol at –20° C. for 5 min. and blocked with 2% goat serum. Antibodies were applied for 1 hour in PBS with 2% serum at room temperature and detected with Alexa fluor 488 donkey anti-rabbit or Alexa fluor 594 goat anti-rat (Molecular Probes). Cells were visualized on a DeltaVision Deconvolution microscope system (Applied Precision). Hippocampal neurons were cultured as previously described. Rather than coculturing with glial cells, neurons were cultured with glial conditioned media. Neurons were visualized with a Nikon TE2000 microscope.

Phosphoinositide assays. Fibroblast phosphoinositides were labelled with myo-[2-$^3$H] inositol, extracted, and quantitated by HPLC. Mouse fibroblasts from the first passage were grown in 100 mm dishes to 60%-70% confluency. The culture was rinsed with PBS and starved for 12 hours in inositol-free DMEM (Tissue culture support center, Washington University, MO) supplemented with 5 g/ml transferrin, 5 g/ml insulin and 10% dialyzed fetal bovine serum. The medium was replaced with labeling medium (inositol-free DMEM containing 5 g/ml transferrin, 20 mM Hepes, and 50 Ci myo-[2-3H] inositol (GE Healthcare, Piscatway, N.J.)). After 24 hours, the culture was treated with 0.6 ml of 4.5% (v/v) perchloric acid for 15 min, scraped off the plate, and spun down at 12,000×g for 10 min at 4° C. The pellet was washed with 0.1 M EDTA once and resuspended in 50 μl deionized water. To deacylate the lipids, samples were transferred to a glass vial, mixed with 1 ml methanol/40% methylamine/n-butanol (4:4:1, v/v) and incubated at 55° C. for 1 hour. The resulting samples were vacuum dried, resuspended in 0.3 ml water and extracted twice with an equal volume of butanol/ethyl ether/formate (20:4:1, v/v). The aqueous phase was vacuum dried and resuspended in 20 μl water. For separation of all isoforms of the glycerophosphoinositides by HPLC, two different elution gradients were used at 1 ml/min flow rate. (pump A: H2O; pump B: 1M $(NH_4)_2HPO_4$, pH 3.8). Gradient 1: 0% B for 5 min; 0-2% B over 15 min; 2% B for 80 min; 2-12% B over 20 min; 12% B for 20 min; 12-80% B over 40 min; 80% B for 20 min; 80-0% B over 5 min. To separate $GroPIns(3,4)P_2$ from $GroPIns(3,5)P_2$, a longer gradient was used: 0% B for 5 min; 0-2% B over 15 min; 2% B for 80 min; 2-10% B over 20 min; 10% B for 65 min; 10-80% B over 40 min; 80% B for 20 min; 80-0% B over 5 min. The positions of GroPIns(3)P, $GroPIns(3,5)P_2$, $GroPIns(3,4)P_2$ and $GroPIns(3,4,5)_3$ were determined by $^{32}P$ labeled standards received as gifts from Dr. Lucia Rameh (Boston Biomedical Research Institute, MA). The positions of GroPIns(4)P and GroPIns(4,5)$P_2$ were confirmed with yeast glycerophoinositide extracts.

Human mutation detection. The cohort of unrelated patients with CMT was previously described (Szigeti et al., Genet Med 8, 86-92 (2006)). The clinical diagnosis was based on clinical examination, electrophysiological studies, and in a few cases, nerve biopsy. All patients received appropriate counseling and gave informed consent approved by the institutional review board. For the initial screen of FIG4, each coding exon was amplified and examined by heteroduplex analysis as previously described (Escayg et al., Nat Genet 24, 343-5 (2000)). The patient mutations were identified by sequencing products exhibiting abnormal mobility. Subsequently, the 23 exons of FIG4 were completely sequenced from the four individuals carrying variants. Genomic DNA from neurological normal control individuals was obtained from the Coriell Institute (panels NDPT006 and NDPT009, 96 samples each) and from a collection of 111 subjects older than 60 years of age without personal or family history of neurological disease (Rainier et al., Arch Neurol 63, 445-7 (2006).

B. Results

Figure 1:
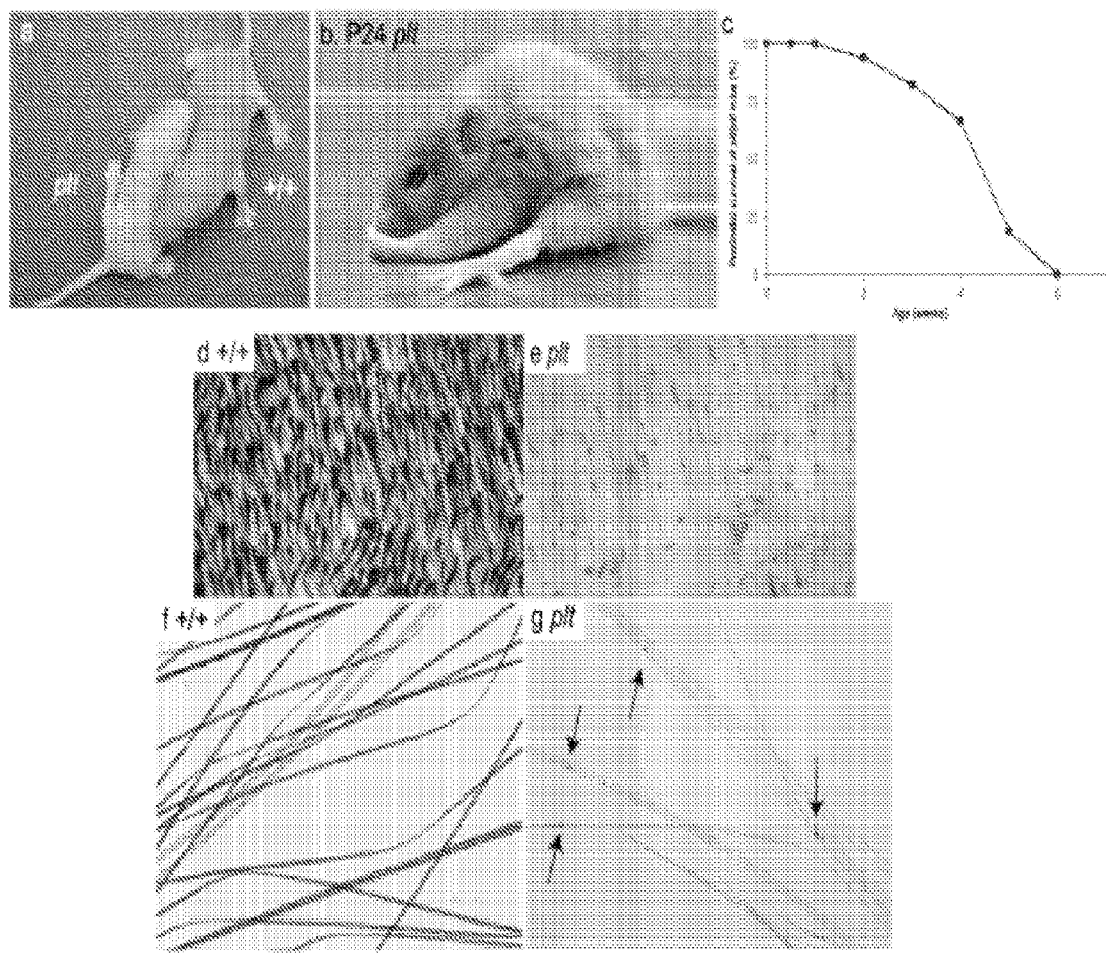
FIG. 1 shows phenotypes of homozygous pale tremor mice. a, Diluted pigmentation at P3. b, Abnormal limb postures at P24. c, Juvenile lethality of F2 mice (n=50). d-e, Skin wholemounts from P10 mice demonstrating pigment-containing hair follicles. f-g, Melanosome clumping in mutant hair shafts (arrows).

Mutant mice with severe tremor, abnormal gait, and diluted pigmentation were detected during a study involving genetic crosses between four inbred strains. One breeding pair generated 25% affected progeny (8/30), consistent with autosomal recessive inheritance of a new mutation now designated pale tremor (plt). Affected animals can be recognized on postnatal day 3 by their diluted pigmentation and small size (FIG. 1a). An intentional tremor develops during the second week of life, and by 3 weeks of age affected animals display abnormal limb postures (FIG. 1b). Progressive loss of mobility and reduction in body weight leads to juvenile lethality.

Figure 2:
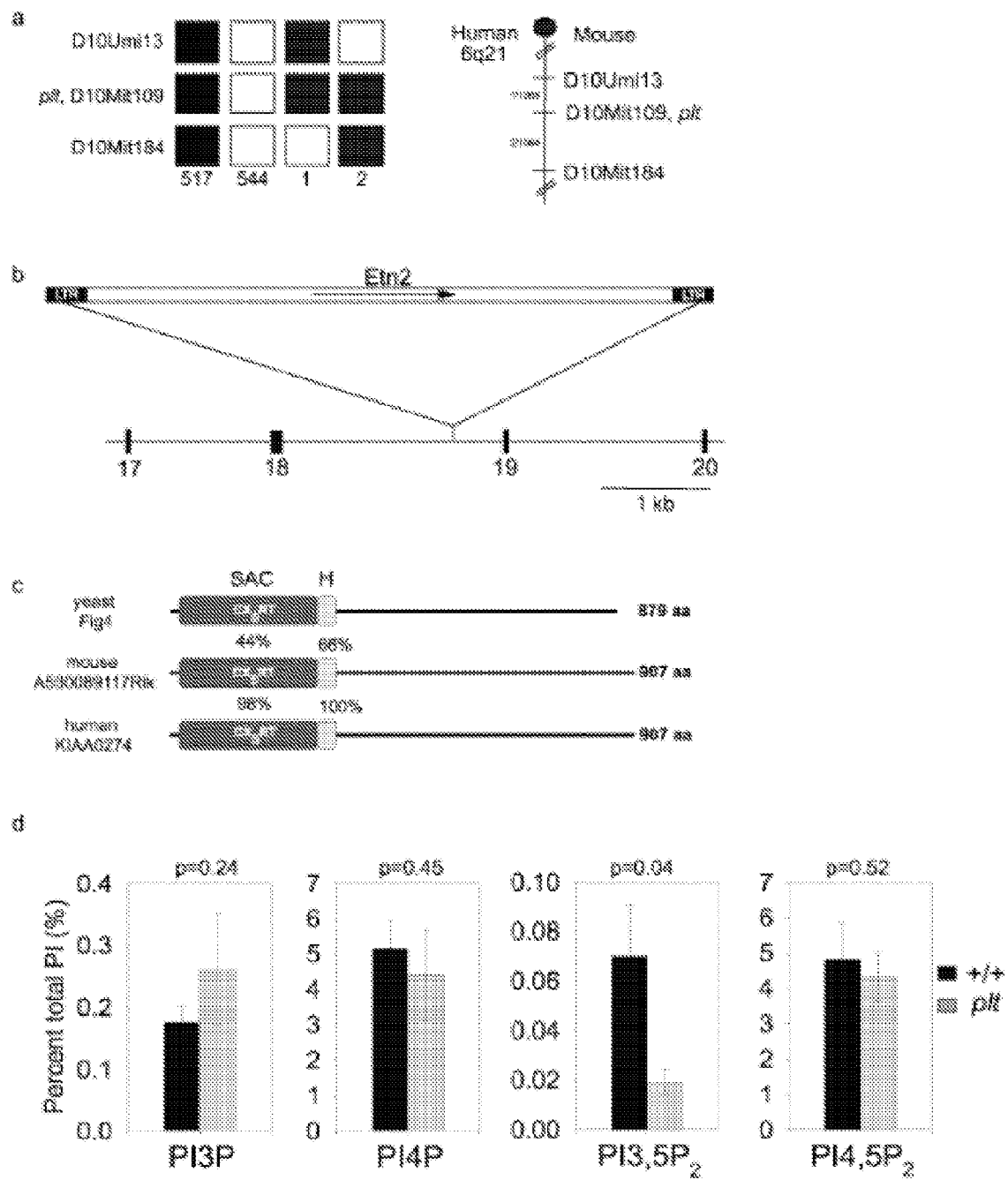
FIG. 2 shows positional cloning of the pale tremor gene. a, Genetic mapping of plt on mouse chromosome 10. The haplotypes of 3 recombinant chromosomes and 1,061 nonrecombinant chromosomes are indicated; solid symbols represent alleles from inbred strains; open symbols represent CAST alleles. b, Location of the inserted Etn2β retrotransposon in intron 18 of the FIG4 gene. c, Protein domains of yeast Fig4p and mammalian homologs. See text for description of the SAC phosphatase domain. d, Altered abundance of the phosphoinositide PI(3,5)P$_2$ in cultured fibroblasts from mutant mice.
Figure 3:
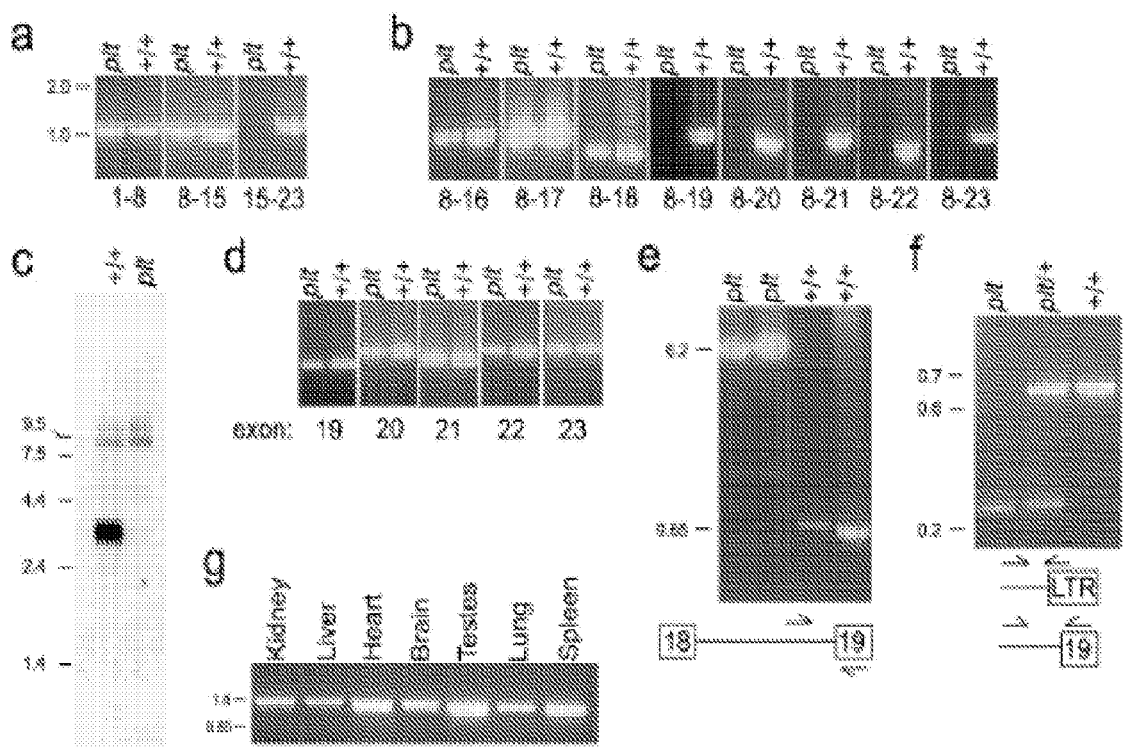
FIG. 3 shows molecular characterization of transcripts and genomic DNA. a, RT-PCR of the FIG4 transcript using forward and reverse primers in the indicated exons with 32 cycles of amplification. b, RT-PCR using a forward primer in exon 8 and a reverse primer in the indicated exon. c, The Northern blot containing 3 ug of brain polyA+ RNA, isolated at P7 prior to extensive neurodegeneration, was hybridized with a 1 kb FIG4 cDNA probe (exons 8 to 15). d, PCR of genomic DNA using primers flanking exons 19 through 23. e, Long-range PCR of genomic DNA using the indicated primers in intron 18 and exon 19. f, Three-primer genotyping assay for the FIG4 plt allele containing the Etn2β insertion. g, RT-PCR of the FIG4 transcript from wildtype tissues; primers located in exon 8 and exon 15.

To genetically map the mutation, a cross was carried out with strain CAST/Ei. The recovery of affected F2 offspring was 9% in this cross (50/532), indicating that there is prenatal loss of some homozygotes on this genetic background. The maximum survival of affected F2 mice was 6 weeks (FIG. 1c). plt was mapped to a 2 Mb interval of mouse chromosome 10 by genotyping 532 F2 animals using microsatellite and SNP markers (FIG. 2a). The nonrecombinant region contained 21 annotated genes, which were tested as candidates by RT-PCR and sequencing. Abnormal results were obtained for the Riken cDNA A530089I17R1k. RTPCR of brain mRNA failed to amplify the distal portion of the transcript (FIG. 3a). Further analysis using a forward primer in exon 8 and a series of reverse primers in exons 16 to 23 demonstrated that the mutant transcript lacks exons 19-23 (FIG. 3b).

A Northern blot was prepared with 3 μg of polyA+ brain RNA isolated at postnatal day 1. Hybridization with a 1 kb cDNA probe containing exons 8 to 15 detected a full length transcript of 3.3 kb in wildtype RNA that was missing from plt RNA (FIG. 3c). No abnormal transcripts were detected in the mutant RNA, even when the exposure time of the X-ray film was increased from 3 hours (FIG. 3c) to 63 hours.

To identify the genomic mutation responsible for loss of expression of exons 19 to 23, PCR of genomic DNA was performed. All of these exons could be amplified from mutant DNA (FIG. 3d), eliminating the possibility of a genomic deletion. The structure of intron 18 was then examined. Using one forward primer in intron 18 with a reverse primer in exon 19, the wildtype product was 0.65 kb in length and the mutant product was 6.2 kb (FIG. 3e). The sequence of the 6.2 kb fragment contained an inserted element of 5,547 by located 384 by upstream of exon 19 (GenBank DQ813648). The inserted element exhibits 99% sequence identity with the consensus for the mouse Etn2β retrotransposon (GenBank Y17106). The retrotransposon is inserted in the same orientation as the interrupted gene and is flanked by a duplication of the hexanucleotoide CCCCTG (FIG. 2b), both of which are characteristic of Etn2β insertions (Maksakova et al., PLoS Genet 2, e2 (2006)). The background strains do not contain an Etn2β element in intron 18, indicating that the plt mutation was caused by retroviral insertion, a common mutational mechanism in the mouse. The mutant allele can be genotyped with a three-primer assay that includes the forward primer in intron 18 and two reverse primers, one in exon 19 and one in the proximal LTR of Etn2β, producing a 646 by wildtype product and a 245 by plt fragment (FIG. 3f). The data are consistent with abnormal splicing from exon 18 to one of the cryptic splice acceptor sites in the Etn2β element3 to generate a low abundance hybrid transcript that is detectable by RT-PCR, but is below the sensitivity of the polyA+ Northern blot. The hybrid transcript would lack exons 19-23 encoding the highly conserved C-terminal 326 amino acid residues that exhibit 92% sequence identity between human and mouse and are likely to be required for protein function.

The original cDNA clone A530089I17Rik was isolated from a T-cell library (Okazaki et al., DNA Res 11, 205-18 (2004)). RTPCR of tissues from wildtype mice demonstrated widespread expression of the plt gene (FIG. 3g), consistent with the information in public EST and microarray databases. In situ hybridization indicates that the transcript is distributed throughout the brain. The human ortholog KIAA0274 is located in a small conserved linkage group on human chromosome 6q21. The mutated protein is most closely related to the yeast SAC-domain phosphatase FIG4, with overall amino acid sequence identity of 35% and sequence similarity of 66% (FIG. 2c). The SAC (suppressor of actin) domain, which contains 7 conserved motifs including the active site sequence CX5R(S/T), is characteristic of phosphatases with specificity for phosphoprotein or phospholipid substrates (Hughes et al., Biochem J 350 Pt 2, 337-52 (2000)). The SAC domain of FIG4 is highly conserved between yeast and human, with 44% amino acid sequence identity (191/435 amino acids). The 4 other mammalian genes with SAC domains (synaptojanin 1, synaptojanin 2, INPP5F and SAC1) all differ from FIG4 by the presence of additional domains and the absence of homology domain H, which is highly conserved in yeast FIG4 and mouse FIG4 (18/29 residues) (FIG. 2c). The sequence comparisons indicate that A530089I17Rik is the mouse homolog of yeast Fig4.

The yeast FIG4 protein is located on the vacuolar membrane. Based on the presence of a Sac domain, FIG4 was predicted to function as a lipid phosphatase. In vitro, Fig4 dephosphorylates the 5-phosphate residue of PI(3,5)P2 (Rudge et al., Mol Biol Cell 15, 24-36 (2004)). Deletion of yeast FIG4 was found to reduce rather than increase the intracellular concentration of PI(3,5)$P_2$ (Duex et al., Eukaryot Cell 5, 723-31 (2006)). Analysis of the yeast mutant fig4-G519R, with an amino acid substitution in the catalytic site of the Sac domain, demonstrated that FIG4 is required for both generation and turnover of PI(3,5)$P_2$ (Duex et al., J Cell Biol 172, 693-704 (2006)). In addition to its lipid phosphatase activity, FIG4 appears to activate the Fab1/PIKfyve kinase that synthesizes PI(3,5)$P_2$ from PI3P, possibly by dephosphorylating the kinase or one of its regulators (Duex et al., J Cell Biol 172, 693-704 (2006). Loss of PI(3,5)$P_2$ in yeast leads to defects in vacuole fission and retrograde traffic from the vacuole to the late endosome (Maksakova, supra; Bonangelino et al., J Cell Biol 156, 1015-28 (2002); Gary et al., Mol Biol Cell 13, 1238-51 (2002)). In mammals, knock-down of Fab1/PIKfyve causes a defect in retrograde traffic from endosomes to the trans-Golgi network 11. In both cases, large vacuoles form. Analysis of phosphoinositides from cultured fibroblasts of pale tremor mice demonstrated a three-fold reduction in PI(3,5)$P_2$ (p=0.04), with no change in 3 other phosphoinositides (FIG. 2d). The data demonstrate that mammalian FIG4 has a conserved biochemical function in metabolism of PI(3,5)$P_2$.

Figure 5:
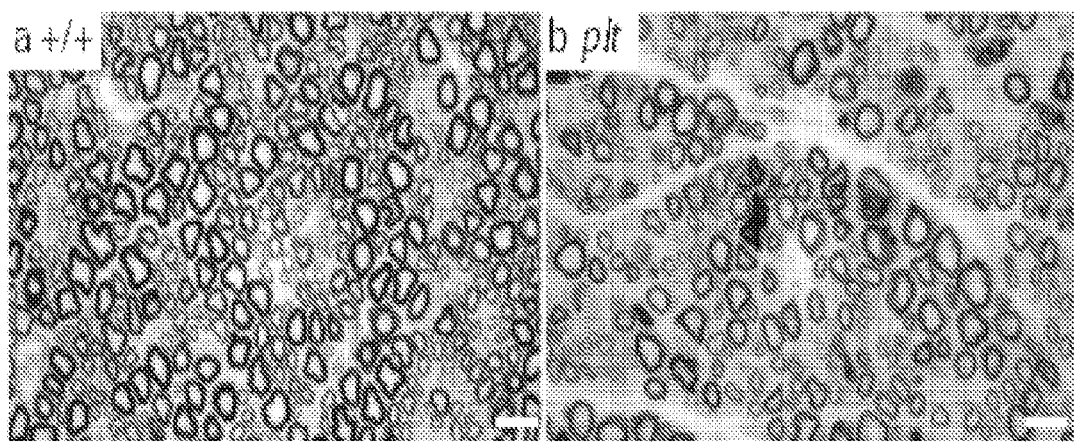
FIG. 5 shows pathological abnormalities in peripheral nerves.
Figure 10:
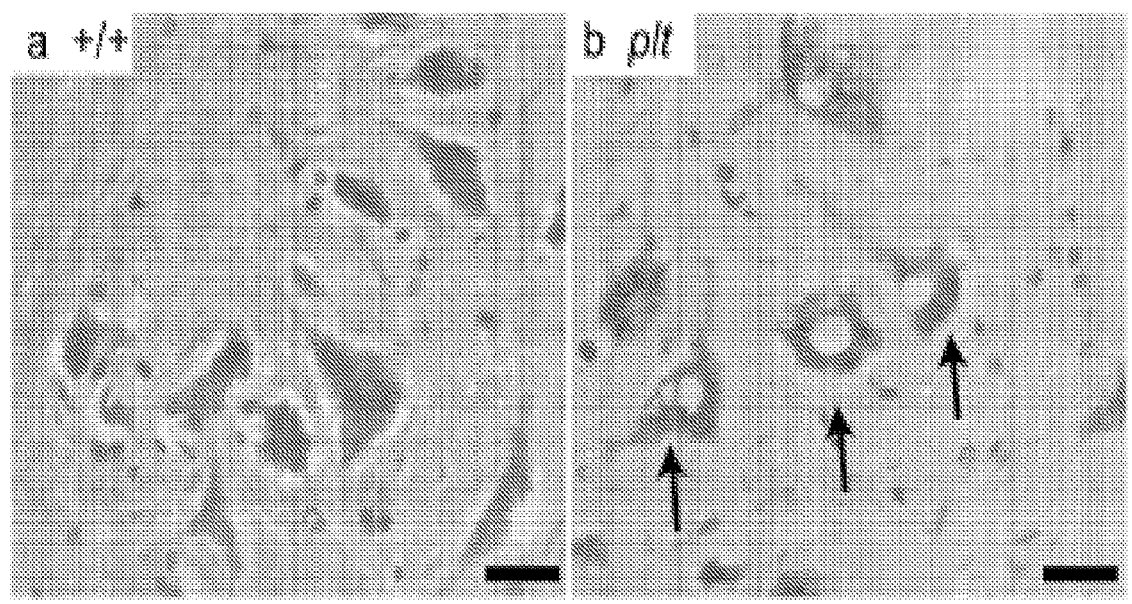
FIG. 10 shows vesicle accumulation in motor neurons. a. Typical motor neurons were visualized in the anterior horn of the spinal cord from wild-type mice. b. In the mutant spinal cord, a majority of motor neurons contained vacuoles scattered in the cytoplasm (arrows), similar to neurons in DRG and brain. Scale bar=25 microns.

A striking pattern of selective neurodegeneration is observed in plt mice. There is extensive loss of neurons from sensory and autonomic ganglia, which occurs prenatally and during the neonatal period (FIG. 4a-e). Neurons filled with enlarged cytoplasmic vesicles are present in the ganglia at this time (FIG. 4 inserts), indicating that vesicle accumulation may preceed cell loss. In contrast, the number of spinal motor neurons appears normal as late as 3 weeks of age (FIG. 4f-g), but cytoplasmic vacuoles become evident by 6 weeks of age (FIG. 10).
Cross-sections of sciatic nerve revealed substantial reduction in the number of large diameter myelinated axons in the mutant (FIG. 5a-b). Nerve conduction studies demonstrated reduced nerve conduction velocity (mutant=11.0±3.4 msec, wildtype=21.5±6.3) and reduced amplitude of compound muscle action potentials (mutant=2.2±1.0 mA; wildtype=5.0±2.1) (mean±SD, n=6 for all values). Decreased amplitude of compound muscle action potentials is consistent with the axonal loss found in the semithin sections of the sciatic nerve and pathological abnormalities in the motor neurons. There was no response when recording from tail sensory fibers, consistent with the severe loss of sensory neurons from the DRG. The neuropathologic and electrophysiological changes in plt mice resemble some human inherited peripheral neuropathies (Schroder, Neuromolecular Med 8, 23-42 (2006); Szigeti et al., Genet Med 8, 86-92 (2006)).

Figure 6:
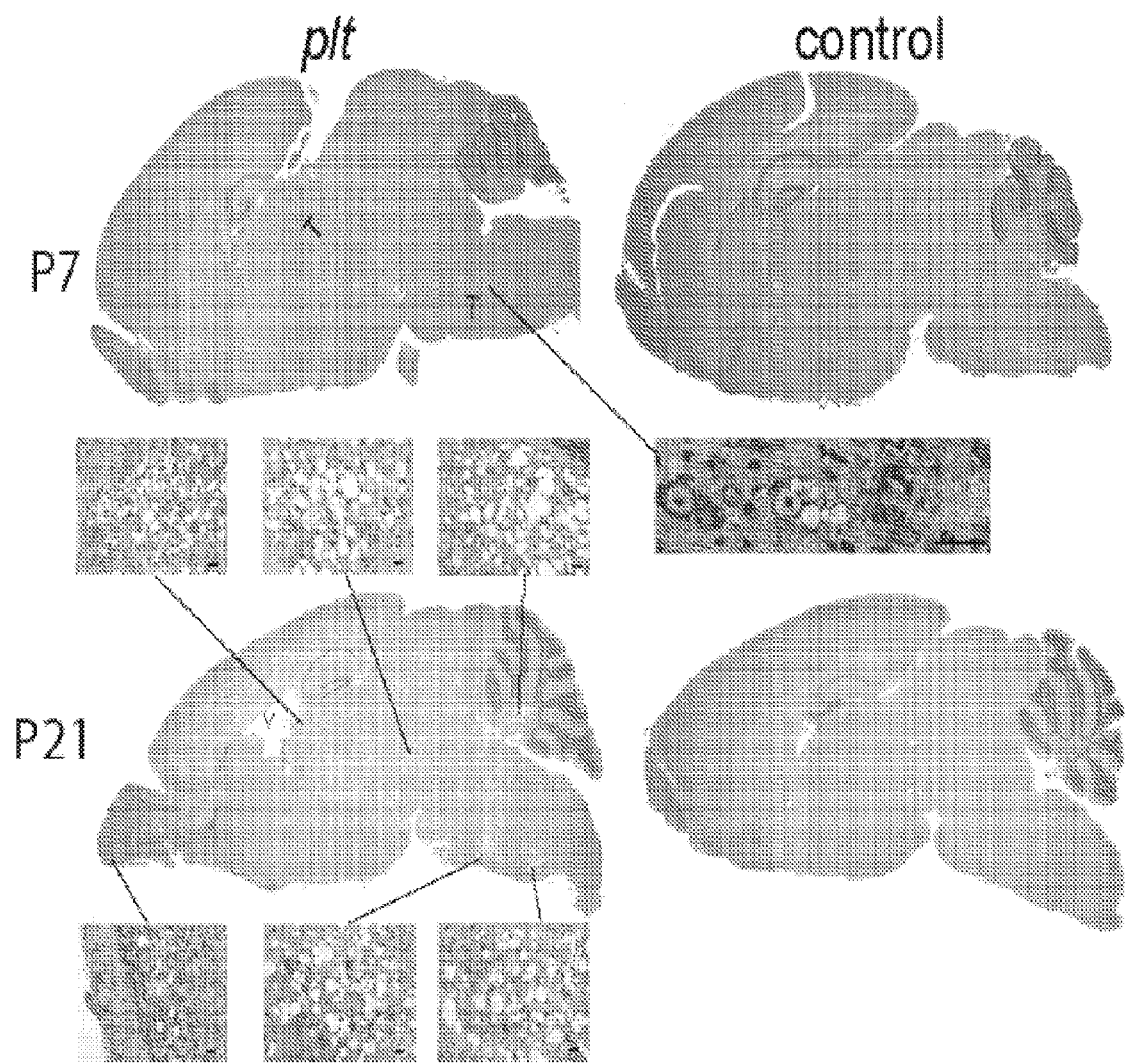
FIG. 6 shows brain degeneration in pale tremor mice. V, ventricle. Scale bars: 25 microns.
Figure 7:
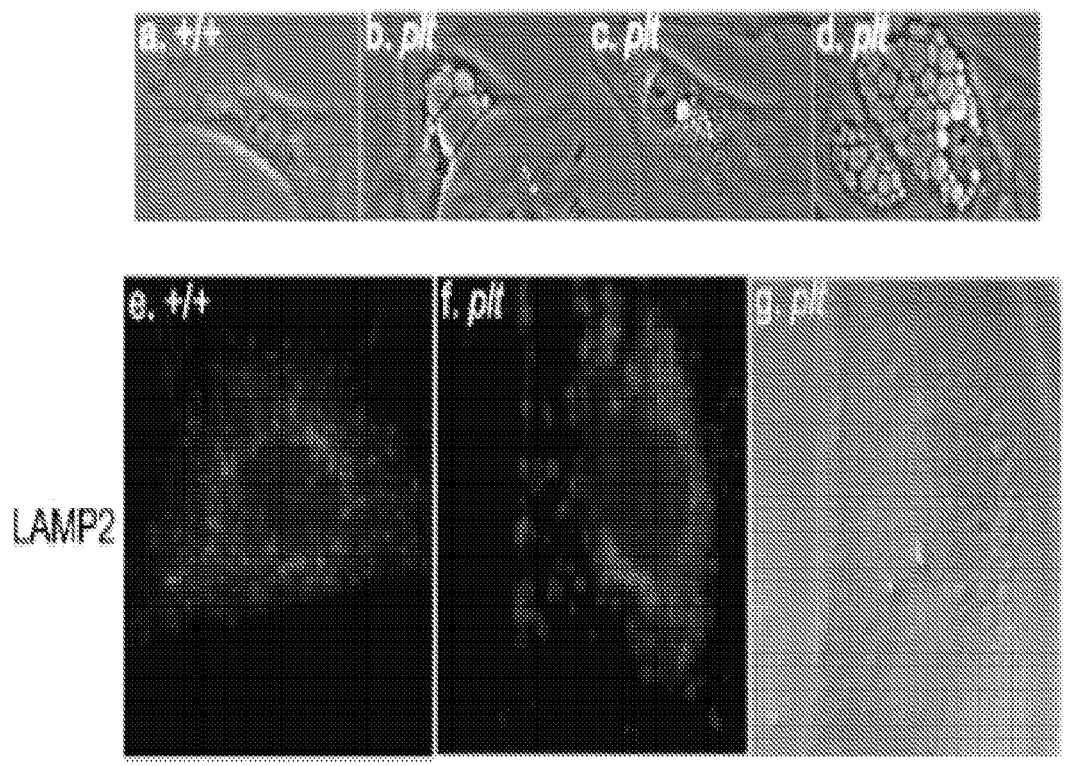
FIG. 7 shows cytoplasmic vesicles in cultured fibroblasts from pale tremor mice. a-d, Mutant fibroblasts are filled with vacuoles. e-g, Membranes of large cytoplasmic vesicles stain with antiserum to LAMP2, a lysosomal membrane protein. Scale bar: 10 μm
Figure 11:
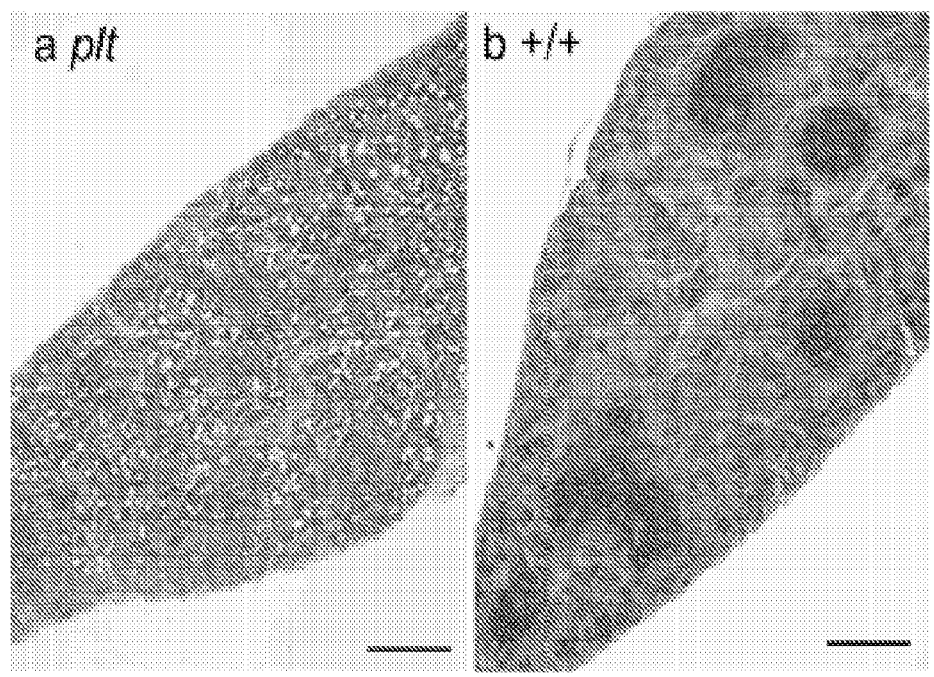
FIG. 11 shows spleen pathology in plt mice plt (a) and wt (b) spleens from 3 week old animals. H&E. scale bar: 250 microns.

Within the brain, small areas of neuronal loss are visible in the thalamus, pons, medulla and deep cerebellar nuclei at 1 week of age, and occasional cell bodies are filled with enlarged vesicles (FIG. 6). These vesicles do not stain with Oil Red 0 (for lipid) or PAS. By 3 weeks of age there is also extensive localized loss of neurons from cortical layers 4 and 5, the deep layers of the superior and inferior colliculus, and the olfactory bulb (FIG. 6). Relatively unaffected regions include the hippocampus, cerebellar cortex, and cerebral cortex layers 1, 2, 3 and 6. Under culture conditions, hippocampal neurons from E16.5 embryos do develop extensive vacuolization (FIG. 4i-l), demonstrating an underlying susceptibility to the mutation. The pattern of regional brain degeneration in vivo does not change between 3 weeks of age and the terminal stage at 6 weeks. Affected brain regions have in common many long projection neurons, which may have an elevated requirement for membrane biosynthesis and axonal vesicle transport. The present invention is not limited to a particular mechanism. Indeed, an understanding of the mechanism is not necessary to practice the present invention. Nonetheless, it is contemplated that the abnormal motor coordination of the plt mutant results from the combined effects of degeneration of DRG neurons resulting in abnormal proprioception, as well as degeneration of neurons from brain regions directly involved in motor control, e.g. layer 5 of the cortex, the thalamus, and the deep cerebellar nuclei. Other affected organs include skin and spleen. Pigment-containing hair follicles are greatly reduced in number in plt skin (FIGS. 1d,e). Clumped melanosomes are visible in the few pigmented hairs (FIGS. 1f,g), similar to other mutants with vesicle disorders (Marks et al., Nat Rev Mol Cell Biol 2, 738-48 (2001)). There is extensive cell loss in spleen (FIG. 11). Circulating white blood cell profiles are normal. Liver, kidney, and testis exhibit normal morphology at the light microscopy level.

In cultures of primary fibroblasts, mutant cells are filled with cytoplasmic vacuoles within the first two days after passage (FIG. 7a-d). Vacuole accumulation was observed in 40% of mutant cells (174/435) compared with 5% of wildtype cells (22/403). The enlarged vesicles in mutant fibroblasts stain positively for the lysosomal membrane protein LAMP2 (FIG. 7 e-g), indicating that the accumulated vesicles represent latestage endosomes.

The plt mutant provides the first information regarding the functional role of mammalian Fig4. The impaired gait, extensive neurodegeneration, and early lethality demonstrate that the mammalian gene is required for neuronal survival. The altered levels of PI(3,5)$P_2$ and PI(3)P in fibroblasts from pale tremor mice demonstrate the role of FIG4 in metabolism of these membrane signaling components. The cellular phenotype of cultured fibroblasts and neurons demonstrate a conserved role for FIG4 in regulation of the size of late endosomes. The rapid degeneration of sensory and autonomic neurons demonstrates their preferential sensitivity to inactivation of Fig4. A similar pattern of neurodegeneration has been observed in a mouse mutant with reduced expression of Vac14, the homolog of a yeast protein that activates Fig4p, supporting the role of P1(3,5)P2 signaling in neurons.

The clinical and pathological features of the peripheral neuropathy in pale tremor mice resemble those of some types of Charcot-Marie-Tooth disease (Schroder et al., Neuromolecular Med 8, 23-42 (2006); Szigeti et al., Genet Med 8, 86-92 (2006)). There have been no reports of familial neuropathies that map to the FIG4 locus on chromosome 6q21. To evaluate the role of FIG4, DNA from 95 unrelated individuals diagnosed with CMT but lacking mutations in the known genes was screened (Szigeti et al., supra). The 23 exons were amplified from genomic DNA, screened by heteroduplex analysis, and sequenced. Mutations were identified in 4 of the 95 patients.

Figure 8:
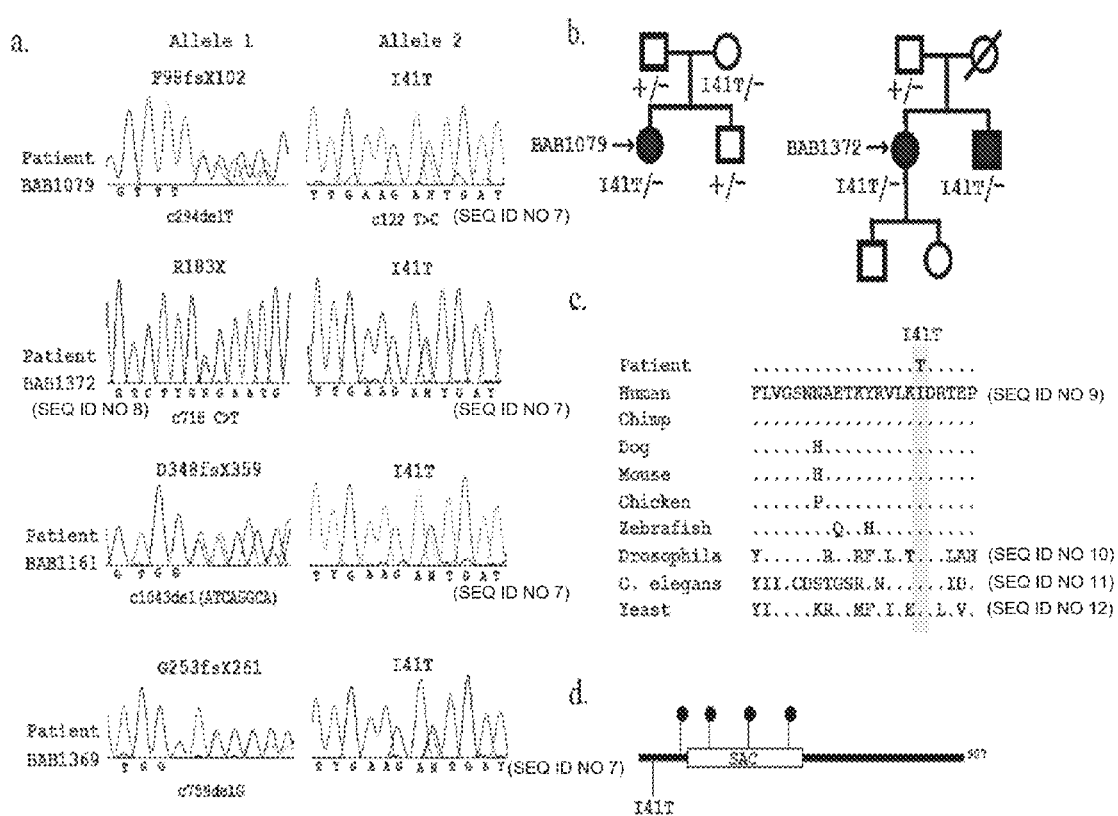
FIG. 8 shows mutations of FIG4 in patients with Charcot-Marie-Tooth disease. a. Sequencing chromatographs for both alleles of four unrelated patients with Charcot-Marie-Tooth disease (CMT). b. Pedigrees for probands BAB1079 and BAB1372 demonstrate inheritance of mutant alleles. c. Evolutionary conservation of the variant residue isoleucine 41 in FIG4 from vertebrate and invertebrate species. d. Location of FIG4 mutations in CMT patients. solid symbols, protein truncation mutations.

A first patient had a severe, early onset disorder. Genotyping demonstrated heterozygosity for the protein truncation mutation F98fsX102 in exon 4 and the missense mutation I41T in exon 2 of FIG4 (FIG. 8a). Each mutation was inherited from a heterozygous parent (FIG. 8b). The unaffected sibling is heterozygous for F98fsX102 only. This pedigree demonstrates autosomal recessive inheritance of CMT. The protein truncation mutation is located in the SAC domain and is likely to inactivate enzymatic activity. The two heterozygous carriers of F98fsX102 in this pedigree are unaffected, indicating that FIG4 does not exhibit haploinsufficiency. Consistent with this conclusion, heterozygous plt+ mice were maintained to 18 months of age without development of abnormal phenotypes.

A second patient is another compound heterozygote, carrying the nonsense mutation R183X in exon 6 and the amino acid substitution I41T in exon 2 (FIG. 8a). The affected sibling inherited both mutations (FIG. 8b). This protein truncation mutation was inherited from the patients' father (FIG. 8b). The mother is an obligate carrier of I41T, but DNA was not available for analysis. The affected siblings exhibit severe clinical features. The patient is functionally quadriplegic. The sibling is wheelchair bound but retains normal use of his arms. Both have slow nerve conduction velocities consistent with de/dysmyelination. A sural nerve biopsy for the sibling demonstrated thinly myelinated nerve fibers and evidence of de- and remyelination. Axonal loss was profound.

Two additional patients (FIG. 8a) were compound heterozygotes and carry unique truncation mutations with the missense mutation I41T (FIG. 8a). The age of onset in these patients was between 1-5 years and nerve conduction velocity was between 2 and 7 m/s (compared with normal values of 40-50 m/s). One patient had motor developmental delay consistent with Dejerine-Sottas neuropathy.

The four patients carry the same missense mutation. Sequencing all 23 exons of FIG4 did not detect additional coding or splice site variants in these patients. Isoleucine 41 is located N-terminal to the SAC phosphatase domain and is evolutionarily invariant in FIG4 from yeast, invertebrate and vertebrate species (FIGS. 8c,d). Sequencing of exon 2 in 295 neurologically normal control individuals did not detect any I41T alleles (0/590 chromosomes in controls, 4/190 chromosomes in CMT patients, p=0.003). There are 3 common haplotypes in the 15 kb region of linkage disequilibrium that extends from intron 1 to intron 3 of FIG4. The haplotypes defined by SNPs rs3799845, rs2025149 and rs7764711 exhibit frequencies of 0.29 (GCG), 0.31 (ATC) and 0.40 (GTC) in the Caucasian population. The I41T variant in exon 2 is carried on the GCG haplotype in the four unrelated Caucasian patients described here (FIG. 12). The Ile 41Thr allele has a calculated LD coefficient D' equal to 1 for rs3799845, rs2025149 and rs7764711, and D' equal to 0.11 for rs4330563 and rs4947022. The haplotype data is consistent with inheritance of a common ancestral mutant allele, rather than a mutation hotspot in exon 2. It is unlikely that I41T is a linkage disequilibrium tag for another deleterious mutation because it has features characteristic of disease mutations: nonconservative substitution of a polar residue for a hydrophobic residue that is invariant from yeast to human, as well as altered protein function in a yeast assay.

Figure 9:
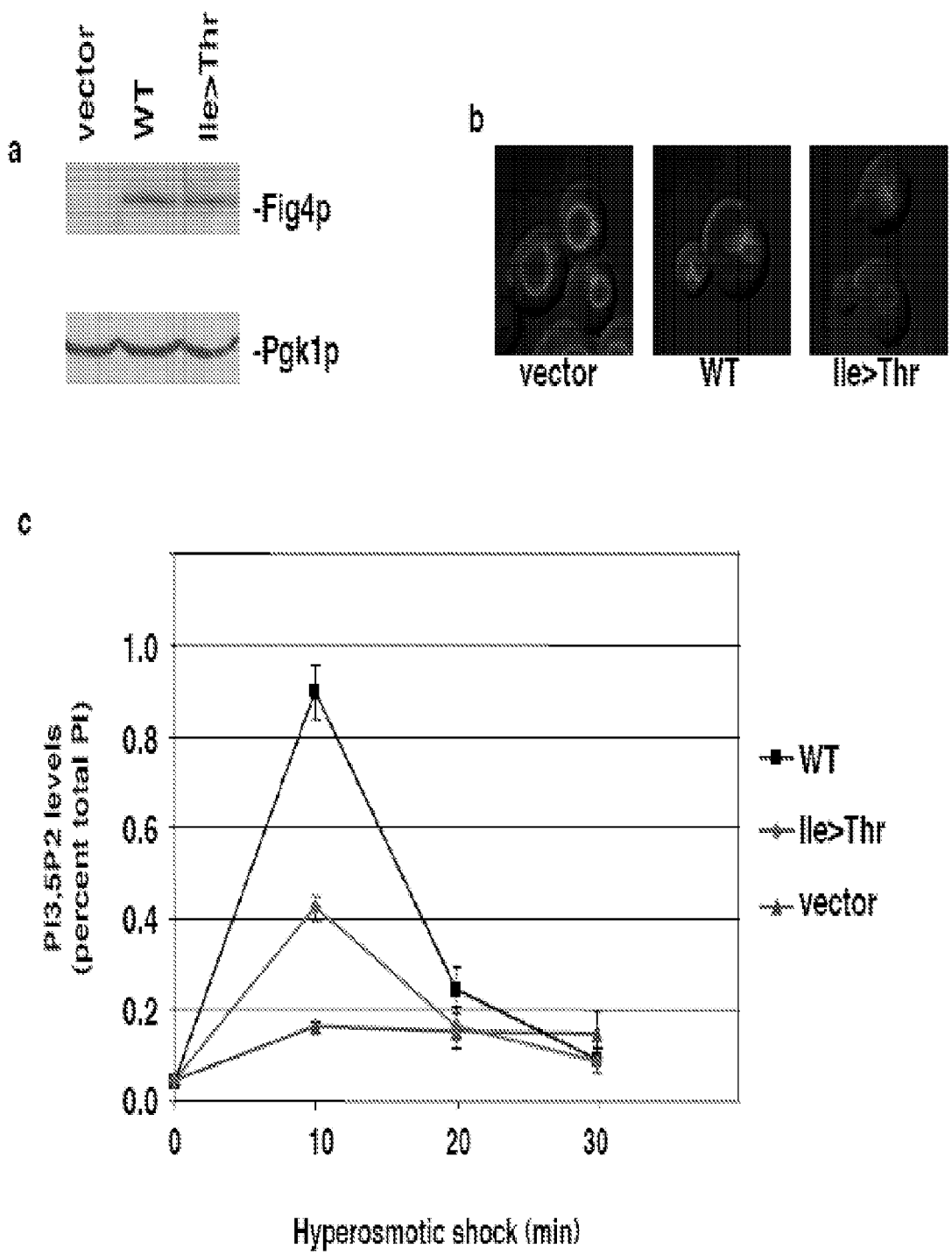
FIG. 9 shows that the FIG4 allele Ile>Thr is defective in activation of yeast Fab1/PIKfyve. a. Western blot analysis with anti-myc antibody demonstrates comparable expression of wildtype and mutant protein. b. Yeast vacuoles were labeled with FM4-64 to assess vacuole volume, an indicator of basal levels of PI(3,5)P2. c. Time course of PI(3,5)P2 levels after hyperosmotic shock to assess the activation of Fab1.

To experimentally evaluate the function of the I41T allele, the corresponding mutation was generated in the conserved isoleucine residue of the yeast protein (FIG. 8e). The function of wildtype and mutant protein were compared in the yeast strain fig4Δ that lacks functional FIG4 (Duex et al., Eukaryot Cell 5, 723-31 (2006)). The expression level of wildtype and mutant protein was comparable on Western blots (FIG. 9a). The enlarged vacuoles in the null background strain reflect the slightly elevated levels of $PI(3,5)P_2$ that results from the absence of FIG4 (FIG. 9b). The enlarged vacuolar size was corrected by wildtype and mutant FIG4 to a comparable extent, indicating that under basal conditions cells expressing the two constructs produce similar levels of $PI(3,5)P_2$ (FIG. 9b). To evaluate the ability of the mutant protein to activate Fab4/PIKfyve, the yeast was treated with hyperosmotic shock as previously described (Duex et al., Eukaryot Cell 5, 723-31 (2006); Duex et al., J Cell Biol 172, 693-704 (2006)). In cells expressing wildtype FIG4, this resulted in a transient 10-fold increase in intracellular $PI(3,5)P_2$ concentration, indicating that Fab1/PIKfyve was properly activated. In cells expressing the mutant FIG4 only a 4-fold increase was observed, demonstrating partial loss of the ability to activate Fab1/PIKfyve. Because the levels of $PI(3,5)P_2$ were low, it was difficult to determine whether the lipid phosphatase activity of the mutant FIG4 was affected.

These data demonstrate that mutation of the FIG4 gene is responsible for peripheral neuronopathy in human patients. The designation CMT4J is utilized for the disorder caused by FIG4 mutations, based on the recessive inheritance. Phosphoinositide signaling has been implicated in other types of peripheral neuropathy. Charcot Marie Tooth type 4B1 is caused by mutations in myotubularin related protein 2 (MTMR2), a 3-phosphatase that can catalyze in vitro dephosphorylation of $PI(3)P$ and $PI(3,5)P_2$ (Begley et al., Proc Natl Acad Sci USA 103, 927-32 (2006); Bolino et al., Nat Genet 25, 17-9 (2000)). Mutations of MTMR2 are predicted to increase the levels of $PI(3,5)P_2$ but the actual effect of these mutations on phosphoinositide levels has not been experimentally determined. The clinical effects of mutations in MTMR2 are much less severe than the FIG4 mutations described here (Bolino et al., J Cell Biol 167, 711-21 (2004); Bonneick et al., Hum Mol Genet 14, 3685-95 (2005)), indicating that these enzymes may function in different subcellular compartments or exhibit distinct substrate specificities in vivo. CMT Type 4B2 is caused by mutations in MTMR13/SBF219, an enzymatically inactive protein that interacts with MTMR2. Other genes that function in vesicle trafficking, including Rab7 and dynamin 2, have recently been associated with inherited neuropathies (Verhoeven et al., Am J Hum Genet 72, 722-7 (2003); Zuchner et al., Nat Genet 37, 289-94 (2005)).

The present study is the first to demonstrate that mutations of FIG4 cause neuropathy in mouse and human, and that loss of FIG4 results in altered levels of $PI(3,5)P_2$ in mammalian cells. The VAC14 protein, which forms a complex with FIG4, is located in synaptic microsomal membrane fractions and interacts with neuronal nitric oxide synthase (Lemaire and McPherson, FEBS Lett (2006)). Evidence indicates a role for endosomal vesicles in delivering membrane components to dendritic spines during long-term potentiation (Park et al., Neuron 52, 817-30 (2006)).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

14451-US-1-PCT_ST25.txt.

What is claimed is:

1. A method of detecting a mutation in a FIG4 gene, comprising: a) contacting a FIG4 gene in a biological sample from a human subject with an oligonucleotide that specifically binds to a mutation in a variant FIG4 nucleic acid under high stringency conditions but does not bind to a FIG4 nucleic acid not comprising a mutation, wherein the oligonucleotide is labeled with a reporter molecule; and b) detecting hybridization of the oligonucleotide to the FIG4 gene, wherein detecting hybridization is indicative of a mutation in a FIG4 gene; wherein said mutation in a variant FIG4 nucleic acid is selected from the group consisting of: a T>C at a position corresponding to position 293 of SEQ ID NO: 1; a C>T at a position corresponding to position 718 of SEQ ID NO: 1; and a deletion of the sequence ATCAGGCA starting at a position corresponding to position 1214 of SEQ ID NO:1.

2. The method of claim 1, wherein said mutation in a variant FIG4 nucleic acid is a T>C at a position corresponding to position 293 of SEQ ID NO: 1.

3. The method of claim 1, wherein said mutation in a variant FIG4 nucleic acid is a C>T at a position corresponding to position 718 of SEQ ID NO: 1.

4. The method of claim 1, wherein said mutation in a variant FIG4 nucleic acid is a deletion of the sequence ATCAGGCA starting at a position corresponding to position 1214 of SEQ ID NO:1.

5. The method of claim 1, wherein said biological sample is selected from the group consisting of a blood sample, a tissue sample, a urine sample, a DNA sample, and an amniotic fluid sample.

6. The method of claim 1, wherein said human subject is selected from the group consisting of an embryo, a fetus, a newborn human, and a young human.

7. The method of claim 1, wherein the reporter molecule is selected from an enzymatic, fluorescent, radioactive and luminescent molecule.

8. A method of detecting a FIG4 gene comprising a first and second mutation, the method comprising: a) contacting a FIG4 nucleic acid in a biological sample from a human subject with a first oligonucleotide that specifically binds to a FIG4 gene comprising a first mutation but does not bind to a FIG4 gene that does not comprise the first mutation, b) contacting a FIG4 nucleic acid in said biological sample with a second oligonucleotide that specifically binds to a FIG4 gene comprising a second mutation but does not bind to a FIG4 gene that does not comprise the second mutation, c) detecting hybridization of the first oligonucleotide with a FIG4 nucleic acid in said biological sample, wherein detecting hybridization is indicative of the presence of the first mutation in the FIG4 gene, wherein the first mutation is a T>C at a position corresponding to position 293 of SEQ ID NO: 1; and d) detecting hybridization of the second oligonucleotide with a FIG4 nucleic acid in said biological sample, wherein detecting hybridization is indicative of the presence of the second mutation in the FIG4 gene, wherein the second mutation is selected from the group consisting of: a deletion of a T at a position corresponding to position 465 of SEQ ID NO:1; a C>T at a position corresponding to position 718 of SEQ ID NO: 1; a deletion of the sequence ATCAGGCA starting at a position corresponding to position 1214 of SEQ ID NO:1; and a deletion of a G at a position corresponding to position 930 of SEQ ID NO:1.

9. The method of claim 8, wherein said second mutation is a deletion of a T at a position corresponding to position 465 of SEQ ID NO: 1.

10. The method of claim 8, wherein said second mutation is a C>T at a position corresponding to position 718 of SEQ ID NO: 1.

11. The method of claim 8, wherein said second mutation is a deletion of the sequence ATCAGGCA starting at a position corresponding to position 1214 of SEQ ID NO: 1.

12. The method of claim 8, wherein said second mutation is a deletion of a G at a position corresponding to position 930 of SEQ ID NO: 1.

13. The method of claim 8, wherein said biological sample is selected from the group consisting of a blood sample, a tissue sample, a urine sample, a DNA sample, and an amniotic fluid sample.

14. The method of claim 8, wherein said human subject is selected from the group consisting of an embryo, a fetus, a newborn human, and a young human.

15. The method of claim 8, wherein at least one of said oligonucleotides is labeled with a reporter molecule.

16. The method of claim 8, wherein the reporter molecule is selected from an enzymatic, fluorescent, radioactive and luminescent molecule.

* * * * *